United States Patent
Choi et al.

(10) Patent No.: US 11,053,295 B2
(45) Date of Patent: *Jul. 6, 2021

(54) PEPTIDES HAVING EFFECTS OF PREVENTING OR TREATING CENTRAL NERVOUS SYSTEM DISEASES AND PHARMACEUTICAL COMPOSITIONS FOR PREVENTING OR TREATING CENTRAL NERVOUS SYSTEM DISEASES CONTAINING SAME AS ACTIVE INGREDIENT

(71) Applicant: IUCF-HYU (INDUSTRY-UNIVERSITY COOPERATION FOUNDATION HANYANG UNIVERSITY), Seoul (KR)

(72) Inventors: Je-Min Choi, Seoul (KR); Sangho Lim, Seoul (KR)

(73) Assignee: IUCF-HYU (INDUSTRY-UNIVERSITY COOPERATION FOUNDATION HANYANG UNIVERSITY), Seoul (KR)

( * ) Notice: Subject to any disclaimer, the term of this patent is extended or adjusted under 35 U.S.C. 154(b) by 218 days.

This patent is subject to a terminal disclaimer.

(21) Appl. No.: 15/753,915

(22) PCT Filed: Aug. 19, 2016

(86) PCT No.: PCT/KR2016/009201
§ 371 (c)(1),
(2) Date: Feb. 20, 2018

(87) PCT Pub. No.: WO2017/034244
PCT Pub. Date: Mar. 2, 2017

(65) Prior Publication Data
US 2019/0202888 A1    Jul. 4, 2019

(30) Foreign Application Priority Data

Aug. 21, 2015   (KR) ..................... 10-2015-0117966
Aug. 19, 2016   (KR) ..................... 10-2016-0105642

(51) Int. Cl.
| | | |
|---|---|---|
| *A61P 25/00* | (2006.01) | |
| *A61P 25/28* | (2006.01) | |
| *A61K 38/00* | (2006.01) | |
| *C07K 14/705* | (2006.01) | |
| *C12N 9/10* | (2006.01) | |
| *C07K 14/005* | (2006.01) | |
| *C07K 14/435* | (2006.01) | |

(52) U.S. Cl.
CPC ........ *C07K 14/70521* (2013.01); *A61P 25/00* (2018.01); *C07K 14/005* (2013.01); *C07K 14/435* (2013.01); *C12N 9/104* (2013.01); *A61K 38/00* (2013.01); *C07K 2319/10* (2013.01); *C12N 2740/16022* (2013.01); *C12N 2740/16033* (2013.01)

(58) Field of Classification Search
None
See application file for complete search history.

(56) References Cited

U.S. PATENT DOCUMENTS

| | | | | |
|---|---|---|---|---|
| 5,786,152 | A | * | 7/1998 | Marengere ....... G01N 33/56972 435/7.1 |
| 2007/0105775 | A1 | | 5/2007 | Lee et al. |
| 2010/0322893 | A1 | | 12/2010 | Franks et al. |

FOREIGN PATENT DOCUMENTS

| | | |
|---|---|---|
| KR | 10-2008-0084937 | 9/2008 |
| KR | 10-2010-0105551 | 9/2010 |
| KR | 10-2014-0046994 | 4/2014 |
| KR | 10-2015-0014443 | 2/2015 |
| WO | 95/33770 | 12/1995 |
| WO | WO 2009/058564 | 5/2009 |
| WO | WO 2013/169338 | 11/2013 |
| WO | WO 2017/034244 | 3/2017 |

OTHER PUBLICATIONS

Weber teaches that (The Oncologist 13: 16-25, 2008).*
Ascherio etal (Nat Rev Neurol 8: 602-612, 2012).*
Brichford C (Everyday Health, 1-13, downloaded from <https://www.everydayhealth.com/multiple-sclerosis/multiple-sclerosis-prevention/> on Sep. 29, 2019).*
Thompson et al (Lancet 391: 1622-1636, 2018).*
Alzheimer's disease—Mayo Clinic, pp. 1-12 < https://www.mayoclinic.org/diseases-conditions/alzheimers-disease/symptoms-causes/syc-2035044>, downloaded on Sep. 29, 2019.*
Choi et al., "Intranasal delivery of the cytoplasmic domain of CTLA-4 using a novel protein transduction domain prevents allergic inflammation", Nature Medicine, vol. 12, No. 5, May 2006: 574-579.
Li et al., "Intracellular Delivery of Molecular Cargo Using Cell-Penetrating Peptides and the Combination Strategies", Int. J. Mol. Sci., 2015, 16:19518-19536.
GenBank: AAF02499.1, cytotoxic T-lymphocyte activated protein 4 [*Homo sapiens*], NCBI, found at https://www.ncbi.nlm.nih.gov/protein/6049193?sat=4&satkey=39333799, 1 page.

(Continued)

*Primary Examiner* — Daniel E Kolker
*Assistant Examiner* — Aditi Dutt
(74) *Attorney, Agent, or Firm* — Sughrue Mion, PLLC

(57) ABSTRACT

The present invention has a function of enabling the penetration of the blood-brain barrier and the blood-spinal cord barrier of the central nervous system, which have not been significantly penetrated, with excellent efficiency, thereby enabling a rapid, quick, and more efficient therapeutic effect to be obtained through low dose administration. In addition, the present invention enables local administration unlike conventional therapeutic agents, thereby decreasing side effects, and enables local administration of a therapeutic agent at a high concentration, thereby enabling potentially new treatments and prescriptions.

8 Claims, 13 Drawing Sheets

Specification includes a Sequence Listing.

(56) References Cited

OTHER PUBLICATIONS

International Search Report for PCT/KR2016/009201, dated Nov. 14, 2016, 6 pages.
Lim et al., "dNP2 is a blood-brain barrier-permeable peptide enabling ctCTLA-4 delivery to ameliorate experimental autoimmune encephalomyelitis", Nature Communications, 6:8244, DOI: 10.1038/ncomms9244, pp. 1-13.

* cited by examiner

PEPTIDES HAVING EFFECTS OF PREVENTING OR TREATING CENTRAL NERVOUS SYSTEM DISEASES AND PHARMACEUTICAL COMPOSITIONS FOR PREVENTING OR TREATING CENTRAL NERVOUS SYSTEM DISEASES CONTAINING SAME AS ACTIVE INGREDIENT

[CROSS-REFERENCE TO RELATED APPLICATION]

This application claims priority to and is a 35 U.S.C. § 371 national phase application of PCT/KR2016/009201 (WO2017/034244), filed on Aug. 19, 2016 entitled "PEPTIDE HAVING EFFECT OF PREVENTING OR TREATING CENTRAL NERVOUS SYSTEM DISEASES AND PHARMACEUTICAL COMPOSITION FOR PREVENTING OR TREATING CENTRAL NERVOUS SYSTEM DISEASES, CONTAINING SAME AS ACTIVE INGREDIENT", which application claims priority to and the benefit of Korean Patent Application No. 10-2015-0117966, filed Aug. 21, 2015 and Korean Patent Application No. 10-2016-0105642, filed Aug. 19, 2016; the disclosures of which is incorporated herein by reference in their entirety.

SEQUENCE STATEMENT

Incorporated by reference herein in its entirety is the Sequence Listing entitled Sequence list ST25,"created Jul. 17, 2018, size of 7 kilobytes.

TECHNICAL FIELD

The present invention relates to peptides having effects of preventing or treating central nervous system diseases and pharmaceutical compositions for preventing or treating central nervous system diseases containing the same as an active ingredient.

BACKGROUND ART

Multiple sclerosis (MS) is a human autoimmune disease which is caused by induction of inflammation in the central nervous system (CNS) by myelin-specific T-cells that cross the protective environment of the blood-brain barrier (BBB). As a mouse model for MS, experimental autoimmune encephalomyelitis (EAE) induced by immunization by $MOG_{35-55}$ and interferon-γ (IFN-γ) or interleukin-17A (IL-17A) that expresses T helper 1 (Th1) or T helper 17 (Th17) cells has been widely researched. Th1 and Th17 cells induce inflammation and necrosis of nerve cells in the central nervous system including the brain and spinal cord and in high levels of these cells.

Although these effecter cells can be potential treatment targets, a number of therapeutic biomolecules cannot be transferred to the central nervous system due to the BBBs and blood-spinal cord barriers (BSCBs) and inevitably thus fail to exhibit therapeutic effects (Non-patent documents 1 and 2).

Thus, a variety of methods to overcome this phenomenon have been developed. However, the developed therapeutic biomolecules are derived from synthetic compounds or other organisms and thus have still problems of failing to exhibit sufficient therapeutic effects due to long-term toxicity or other side effects as well as limitation of penetration by the BBBs and BSCBs.

For example, conventional patent documents associated with penetrants or drug carriers based on peptides to improve penetration to blood-brain barriers have been reported. For example, Korean Patent No. 10-0242597 discloses a blood-brain barrier penetrant that includes peptides having an amino acid sequence of $NH_2$-arginine-proline-hydroxyproline-glycine-thienylalanine-serine-proline-4-Me-tyrosine $(CH_2NH)$-arginine-COOH or a structural analogue with a predetermined modification thereof (Patent Document 1), and Korean Patent Laid-open No. 10-2014-0026372 discloses an amino acid sequence represented by a predetermined sequence list and having the capability to penetrate the blood-brain barrier (Patent Document 2).

DISCLOSURE

Technical Problem

Therefore, the present invention has been made in view of the above problems, and it is one object of the present invention to provide peptides that are effectively capable of passing through the blood-brain barrier or blood-spinal cord barrier and have excellent inhibitory activity against IL-2, pharmaceutical compositions containing the same and methods for preventing or treating diseases using the same.

Technical Solution

In accordance with the present invention, the above and other objects can be accomplished by the provision of a peptide with inhibitory activity against IL-2 having an amino acid sequence represented by Sequence ID No. 1.

In accordance with another aspect of the present invention, provided is a peptide with inhibitory activity against IL-2 including a fragment of the cytoplasmic domain in the CTLA-4 protein represented by Sequence ID No. 2 or 3, or a fusion peptide of two or more of the fragment.

The fusion peptide may have an amino acid sequence represented by Sequence ID No. 4.

In accordance with another aspect of the present invention, provided is a fusion product including a peptide having an amino acid sequence represented by Sequence ID No. 1, a fragment thereof, or a fusion peptide of two or more of the fragment, and a cell-penetrating peptide.

The fragment may have an amino acid sequence represented by Sequence ID No. 2 or Sequence ID No. 3.

The fusion peptide may have an amino acid sequence represented by Sequence ID No. 4.

The cell-penetrating peptide may include any one selected from the group consisting of HIV-1 tat (47-57), D-amino acid-substituted HIV-1 tat (47-57), arginine-substituted HIV-1 tat (47-57), *Drosophila* Antennapaedia (43-58), virus RNA-bound peptides including 7 or more amino acids, DNA-bound peptides including 7 or more arginines, polyarginine polypeptides including 6 to 8 arginines, polypeptides including 7 to 11 lysines, dNP2 proteins having an amino acid sequence represented by Sequence ID No. 5, Hph-1 (Sequence ID No. 6), Transportan (Sequence ID No. 8), Pep-1 (Sequence ID No. 9), pVEC (Sequence ID No. 10), M918 (Sequence ID No. 11), TP10 (Sequence ID No. 12), VP22 (Sequence ID No. 13), Buforin 2 (Sequence ID No. 14), KALA (Sequence ID No. 15), CL22 (Sequence ID No. 16) and Crotamine (Sequence ID No. 17).

The cell-penetrating peptide may be a dNP2 protein of the amino acid sequence represented by Sequence ID No. 5.

In accordance with another aspect of the present invention, provided is a recombinant expression vector including genes encoding the fusion product.

In accordance with another aspect of the present invention, provided is a pharmaceutical composition for preventing or treating a central nervous system disease including the fusion product as an active ingredient.

The cell-penetrating peptide in the fusion product may have an activity to penetrate the blood-brain barrier or blood-spinal cord barrier.

The central nervous system disease may include any one selected from the group consisting of spinal cord damage, stroke, cerebral infarction, cerebral ischemia, Alzheimer's disease and multiple sclerosis.

In accordance with yet another aspect of the present invention, provided is a method for preventing or treating central nervous system diseases in animals excluding humans by administrating the pharmaceutical composition to a subject.

Effects of the Invention

In accordance with the present invention, it is possible to achieve more efficient treatment effects more rapidly in even lower doses with the function to highly efficiently penetrate the blood-brain barrier and blood-spinal cord barrier of the central nervous system, which could not be significantly permeated in the past and, at the same time, IL-2 inhibitory activity.

In addition, compared to conventional therapeutic agents, the present invention can reduce side effects due to possible local administration and can provide potentially new treatments and prescriptions owing to possible local administration of high concentrations of therapeutic agents.

BRIEF DESCRIPTION OF THE DRAWINGS

The above and other objects, features and other advantages of the present invention will be more clearly understood from the following detailed description taken in conjunction with the accompanying drawings, in which.

BEST MODE

Figure 1A:
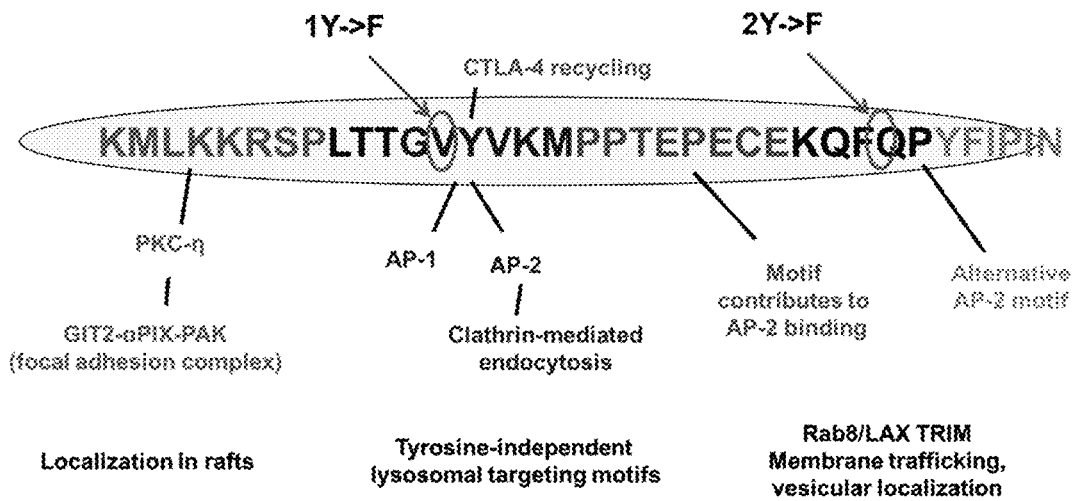
FIG. 1A shows identification results of a fragment of the cytoplasmic domain in the CTLA-4 protein according to the present invention and variation parts.
Figure 1B:
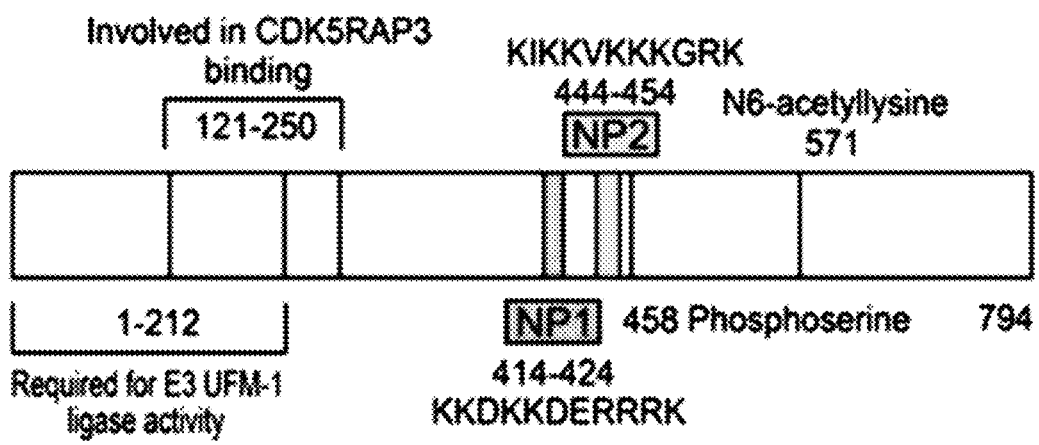
FIG. 1B shows identification results of dNP2, a human-derived cell-penetrating peptide according to the present invention.

Hereinafter, several aspects and various embodiments of the present invention will be described in more detail.

Central nervous system (CNS)-invasive effecter T-cells are known to play a pivotal role in the development and progression of multiple sclerosis (MS). However, drugs associated with MS developed to date are very limited. The reason for this is that it is considerably difficult to transfer these drugs to the CNS and thereby regulate the invasive T-cells.

Therefore, the present invention has been completed based on repeated attempts to overcome the aforementioned problem of the conventional drugs and develop novel proteins that are associated with central nervous system diseases and have excellent ability to penetrate the brain-blood barriers or brain-spinal cord barriers that are densely organized.

One aspect of the present invention is directed to a peptide with inhibitory activity against IL-2 having an amino acid sequence represented by Sequence ID No.

One feature of the present invention is to develop novel proteins that have excellent ability to penetrate the brain-blood or spinal cord-blood barrier, which could not be easily introduced into cells and suppress the activity of T-cells (in particular, Th17) and thereby alleviate the cause of diseases derived from autoimmunity, thus preventing or treating central nervous system diseases.

As used herein, the term "peptide with inhibitory activity against IL-2 having an amino acid sequence represented by Sequence ID No. 1" refers to a sequence derived from the cytoplasmic domain in a CTLA-4 protein, which is obtained by sequencing only a part of the exon 4 of whole CTLA-4 protein derived from humans or mice. That is, it means an amino acid sequence of a part that has an identity of 100% among amino acid sequences of CTLA-4 proteins in humans and mice. Such an amino acid sequence has a low risk of causing side effects such as immune reaction when applied to humans.

The peptide with inhibitory activity against IL-2 having an amino acid sequence represented by Sequence ID No. 1 is a fragment of CTLA-4 that has inhibitory activity on expression of IL-2 in the CTLA-4 protein, which has the effect of passing through the central nervous system, that is, the blood-brain barrier or blood-spinal cord barrier in a high efficiency. By using an amino acid sequence that has an identity of 100% in humans and animals (mice) except humans, the fragment can be applied to both of them.

Specifically, the peptide with inhibitory activity against IL-2 having an amino acid sequence represented by Sequence ID No. 1 refers to a peptide including the $188^{th}$ amino acid residue to the $213^{th}$ amino acid sequence of the cytotoxic T lymphocyte antigen-4 (CTLA-4) protein (Sequence ID No. 1), which is hereinafter referred to as "ctCTLA-4". The peptide is a polypeptide, the N-end and C-end of which are partially deleted, in order to provide penetration ability to the blood-brain barrier or blood-spinal cord barrier as well as preventive or therapeutic effects.

Another aspect of the present invention is directed to a peptide with inhibitory activity against IL-2 including a fragment of the cytoplasmic domain in the CTLA-4 protein represented by Sequence ID No. 2 or 3, or a fusion peptide of two or more of the fragment.

The fragment of the ctCTLA-4 protein includes the $201^{st}$ amino acid residue to the $210^{th}$ amino acid sequence (Sequence ID No. 2), or the $218^{th}$ amino acid residue to the $223^{th}$ amino acid sequence of the ctCTLA-4 protein (Sequence ID No. 3), and may be a fragment of the polypeptide, the N- and C-end of which are partially deleted, in order to provide penetration ability to the blood-brain barrier or blood-spinal cord barrier as well as preventive or therapeutic effects.

The fusion peptide may be an amino acid sequence represented by Sequence ID No. 4 wherein the Sequence ID No. 2 is combined with the Sequence ID No. 3.

The peptide with inhibitory activity against IL-2 is very small and thus has an advantage of minimizing possible biological interference.

The peptide with inhibitory activity against IL-2 may be naturally extracted, or synthesized, or produced by genetic recombination, based on DNA sequence.

The following various test results showed that the ctCTLA-4 peptide is capable of highly efficiently passing through the central nervous system, that is, the blood-brain barrier or blood-spinal cord barrier and has the effect of inhibiting the activity of T-cells (in particular, Th17) causing central nervous system diseases.

In other words, the peptide with inhibitory activity against IL-2 derived from the CTLA-4 protein has effects of improving transfer to the central nervous system and penetration through the blood-brain barrier and blood-spinal cord barrier, and of suppressing T-cells excellent in the multiple sclerosis animal model. Accordingly, the peptide with inhibitory activity against IL-2 according to the present invention can be used for the prevention or treatment of central nervous system diseases.

Another aspect of the present invention is directed to a fusion product including: a peptide having an amino acid sequence represented by Sequence ID No. 1, a fragment thereof or a fusion peptide of two or more of the fragment; and a cell-penetrating peptide.

The peptide having an amino acid sequence represented by Sequence ID No. 1, a fragment thereof or a fusion peptide of two or more of the fragment has been described above and detailed explanation thereof is thus omitted.

In an embodiment of the present invention, the cell-penetrating peptide is further introduced into one or two sides of the peptide having an amino acid sequence represented by Sequence ID No. 1, a fragment thereof or a fusion peptide of two or more of the fragment, so that penetration ability into the central nervous system blood vessels can be further improved. Such a fusion product may be referred to as "fusion protein" as well.

The fusion product down-regulates production of cytokines in activated T-cells and shows inhibitory effects in both preventive and therapeutic models of experimental autoimmune encephalomyelitis (EAE), thus causing decreases in demyelination and the numbers of CNS-invasive T helper 1 (Th1) and T helper 17 (Th17) cells.

The term "fusion product" or "fusion protein", as used herein, includes ctCTLA-4 peptides, fragments thereof or fusion peptides, and cell-penetrating peptides, and means covalently bonded composites formed by genetic fusion or chemical bonding thereof.

In addition, the term "genetic fusion", as used herein, means binding created by linear or covalent bonding through generic expression of DNA sequences encoding proteins.

In an embodiment of the present invention, the cell-penetrating peptide may be any one selected from the group consisting of HIV-1 tat (47-57), D-amino acid-substituted HIV-1 tat (47-57), arginine-substituted HIV-1 tat (47-57), Drosophila Antennapaedia (43-58), virus RNA-bound peptides including 7 or more amino acids, DNA-bound peptides including 7 or more arginines, polyarginine polypeptides including 6 to 8 arginines, polypeptides including 7 to 11 lysines, dNP2 proteins having an amino acid sequence represented by Sequence ID No. 5, Hph-1 (Sequence ID No. 6), Transportan (Sequence ID No. 8), Pep-1 (Sequence ID No. 9), pVEC (Sequence ID No. 10), M918 (Sequence ID No. 11), TP10 (Sequence ID No. 12), VP22 (Sequence ID No. 13), Buforin 2 (Sequence ID No. 14), KALA (Sequence ID No. 15), CL22 (Sequence ID No. 16) and Crotamine (Sequence ID No. 17).

Most cell-penetrating peptides are known to have excellent in vitro penetration efficiency in a variety of cell lines and are predicted to have improved cell penetration ability when bound to cargo proteins. However, in general, the cell-penetrating peptides were found to have much poorer penetration efficiency to primary cells. For this reason, cell-penetrating peptides have been greatly restricted in clinical application in humans (Simon, M. J., Gao, S., Kang, W. H., Banta, S. & Morrison, B., 3rd. TAT-mediated intracellular protein delivery to primary brain cells is dependent on glycosaminoglycan expression. Biotechnology and bioengineering 104, 10-19, doi:10.1002/bit.22377 (2009)). On the other hand, the present invention demonstrates that the effects of clinical application to humans, which could not be conventionally expected, can be significantly improved by combining, with cell-penetrating peptides, ctCTLA-4 proteins or fragments thereof having penetration ability to the central nervous system, in particular, the blood-brain barrier or blood-spinal cord barrier. In particular, when the cell-penetrating peptide is a dNP2 protein having an amino acid sequence represented by Sequence ID No. 5, penetration ability to the blood-brain barrier or blood-spinal cord barrier is found to be significantly improved.

Another aspect of the present invention is directed to a recombinant expression vector that includes genes encoding the fusion product, or a recombinant expression vector that includes genes encoding the peptide with inhibitory activity against IL-2 and genes encoding the cell-penetrating peptide.

The recombinant expression vector may include sequences (Sequence ID No. 1, 2, 3 or 4) of the cell-penetrating peptide and the peptide with inhibitory activity against IL-2, and a tag sequence to facilitate purification of the fusion product, for example, a continuous histidine codon, a maltose-binding protein codon, a Myc codon or the like, and may further include a partner or the like to improve solubility of the fusion product. In addition, the recombinant expression vector may include a spacer amino acid or base sequence to stabilize the whole structure and functions of the recombinant protein, or to provide flexibility to proteins that respective genes encode. Examples of the spacer include AAY (P. M. Daftarian et al., J Trans Med 2007, 5:26), AAA, NKRK (R. P. M. Sutmuller et al., J Immunol. 2000, 165: 7308-7315), or a plurality of lysine residues in one thereof (S. Ota et al., Can Res. 62, 1471-1476, K. S. Kawamura et al., J Immunol. 2002, 168: 5709-5715), but the present invention is not limited thereto. In addition, the recombinant expression vector may include a sequence that is specifically cleaved by an enzyme in order to remove an unnecessary part of the recombinant protein, an expression regulatory sequence, and a marker or reporter gene sequence to identify transfer into cells, but the present invention is not limited thereto.

The expression regulatory sequence used for the recombinant expression vector may be composed of regulatory domains that include promoters specific to cells, tissues or organs which target DNAs and/or RNAs are selectively transferred to or expressed in.

The fusion product according to the present invention may be used as an active ingredient for a preventive or therapeutic pharmaceutical composition. This composition can be a therapeutic agent effective for treatment of a central nervous system inflammatory disease.

The central nervous system disease may be any one selected from the group consisting of spinal cord damage, stroke, cerebral infarction, cerebral ischemia, Alzheimer's disease and multiple sclerosis, but the present invention is not limited thereto.

The composition according to the present invention may further include an appropriate carrier, excipient and diluent which are generally used in preparation of pharmaceutical compositions. The pharmaceutical composition according to the present invention can be formulated for use in the form of oral formulations, external preparations, suppositories and sterile injection solutions such as powders, granules, tablets, capsules, suspensions, emulsions, syrups and aerosols according to an ordinary method.

Suitable preparations known in the art are preferably those disclosed in Remington's Pharmaceutical Science (Mack Publishing Company, Easton Pa.).

Examples of the carrier, excipient and diluent, which may be included in the pharmaceutical composition according to the present invention, may include lactose, dextrose, sucrose, sorbitol, mannitol, xylitol, erythritol, maltitol, starch, acacia gum, alginate, gelatin, calcium phosphate, calcium silicate, cellulose, methylcellulose, microcrystalline cellulose, polyvinylpyrrolidone, water, methyl hydroxybenzoate, propyl hydroxybenzoate, talc, magnesium stearate and mineral oil. The preparations can be produced using generally used diluents or excipients such as fillers, extenders, binders, wetting agents, disintegrants and surfactants. Solid preparations for oral administration include tablets, pills, powders, granules, capsules and the like. These solid preparations are produced by mixing the extract with at least one excipient, for example, starch, calcium carbonate, sucrose, lactose, gelatin or the like. In addition, apart from the simple excipient, lubricants such as magnesium stearate and talc may be used. Liquid preparations for oral administration include suspensions, liquids for internal use, emulsions, syrups and the like. Generally used diluents such as water and liquid paraffin as well as various excipients, for example, wetting agents, sweeteners, fragrances, preservatives and the like may be included. Preparations for parenteral administration include sterile aqueous solutions, non-aqueous solvents, suspensions, emulsions, lyophilized preparations and suppositories. Useful non-aqueous solvents and suspensions include propylene glycol, polyethylene glycol, vegetable oil such as olive oil, injectable ester such as ethyl oleate and the like. The base for suppositories includes Witepsol, Macrogol, Tween 61, cacao butter, laurin, glycerogelatin or the like. The term "administration" as used herein means providing the predetermined composition according to the present invention with a subject by any suitable method.

The preferred dose of the pharmaceutical composition according to the present invention can be suitably selected by those skilled in the art according to patient's conditions and body weight, severity of disease, dosage form, and administration route and period. In order to achieve desired effects, the composition of the present invention can be administrated daily at a dose of 0.001 to 1000 mg/kg. The composition can be administered in a single dose per day or in multiple doses per day. The dose should not be construed as limiting the scope of the present invention in any context.

The pharmaceutical composition according to the present invention can be administered via various routes. All administration methods can be used, for example, orally, rectally or by intravenous, intramuscular, subcutaneous, intrauterine, intradural or intracerebroventricular injection.

Also, the present invention provides a food composition for preventing or alleviating central nervous system diseases containing, as an active ingredient, the fusion product.

When the composition according to the present invention is used as a food additive, it may be added alone or may be used in combination with other foods or food ingredients, and may be suitably used according to conventional methods. The amount of active ingredient added can be suitably determined depending on purpose of use (prophylactic, health or therapeutic treatment). When the composition according to the present invention is used for the preparation of a food or beverage, it is generally added in an amount of 15 wt % or less, preferably 10 wt % or less, based on the total weight of the food or beverage. However, when prolonged intake is intended for the purpose of health, hygiene or health control, the amount of the active ingredient may be smaller than the lower limit of the range defined above. In addition, the active ingredient may be used in an amount higher than the upper limit of the above range because it does not cause a problem in terms of safety.

In addition to the ingredients described above, the composition according to the present invention may include a variety of nutrients, vitamins, electrolytes, flavors, colorants, pectic acid and salts thereof, alginic acid and salts thereof, organic acids, protective colloidal thickening agents, pH adjusting agents, stabilizers, antiseptics, glycerine, alcohol and carbonating agents for carbonated drinks. Further, the composition according to the present invention may include flesh for producing natural fruit juices, fruit juice drinks and vegetable drinks. This ingredient may be used alone or in combination. The proportion of this additive is not significantly important, but is generally determined within the range of 0.01 to 0.1 parts by weight with respect to 100 parts by weight of the composition according to the present invention.

Another aspect of the present invention is directed to a method for preventing or treating central nervous system diseases in animals excluding humans by administrating the pharmaceutical composition to a subject.

The pharmaceutical composition can be injected in vivo or in vitro via a route such as intravenous, intraperitoneal, intramuscular, subcutaneous, intradermal, nasal, mucosal, inhalation or oral route. The application of the transfer mode can be sufficiently expanded to transfer to culture cells as well as general in vivo transfer, that is, transfer to animal cells and animal tissues and animals.

There is no limitation as to plasmid size because the pharmaceutical composition is non-immunogenic and non-infectious and DNAs are not packaged in vector organisms such as retroviral or adenovirus vector organisms. Accordingly, the pharmaceutical composition can be also used for any recombinant gene expression structure with a practical size.

Hereinafter, the present invention will be described in more detail with reference to examples. However, the disclosure including the following examples should not be construed as confining or limiting the scope and content of the present invention. In addition, it is obvious that those skilled in the art can easily implement the present invention that does not specifically suggest experimental results so long as it is based on the disclosure including the following examples, and that these alterations and modifications fall within the scope of the claims.

MODE FOR INVENTION

Test Method

1) Cell Lines and Cell Culture

Jurka T-cells (human leukemia cells) were purchased from the American Type Culture Collection (ATCC) and stored in Roswell Park Memorial Institute (RPMI) 1640 medium supplemented with 10% fetal bovine serum (FBS) and 1% penicillin/streptomycin antibiotics. HeLa cells (human cervical cancer cells) were purchased from the ATCC and cultured in Dulbecco's modified Eagle's media (DMEM) containing GlutaMAX supplemented with 10% fetal bovine serum (FBS) and 1% penicillin/streptomycin antibiotics. All cells were stored at 37° C. in a 5% carbon dioxide incubator. The aforementioned reagents were purchased from Thermo Scientific HyClone.

2) Mice 6 to 8 week-old female C57BL/6 mice were purchased from the Orient Bio (Daejeon, Korea). The mice were bred and stored in a specific aseptic facility at Hanyang University, and regularly fed with food and sterilized water under constant conditions of predetermined temperature (21±1° C.) and humidity (50±5%) and 12-hour bright/dark cycles. All animal protocols used in the present invention were approved by the Institutional Animal Care and Use Committee of Hanyang University.

3) In Vitro Transfer Efficiency

Jurkat T-cells were cultured at a density of $5.0 \times 10^5$ cells/well on a 24-well plate in RPMI 1640 medium. After the cells were seeded, respective proteins were added at designated times. After culturing, the cells were collected and washed three times with phosphate buffered saline (PBS). Intracellular fluorescence was analyzed with a fluorescence-activated cell sorting (FACS) Canto II flow cytometer (BD Bioscience) and data were analyzed using FlowJo software (Tree Star, INC.). The spleen isolated from the 6-week-old C57BL/6 mice were loaded on a 60×15 mm cell culture dish containing 3 ml of PBS. A single cell suspension was physically prepared using a cell strainer having pores with a size of 0.45 μm, 10 ml of fresh PBS was added thereto and the resulting mixture was centrifuged.

Erythrocyte cells were dissolved in an ACK buffer solution (0.15 M $NH_4Cl$, 10 mM $KHCO_3$, 1 mM EDTA-2Na, pH 7.2). After $1.0 \times 10^6$ spleen cells were seeded on each well, transfer efficiencies of the proteins according to the present invention were investigated. The cells were stained with anti-mouse CD4-PerCP-Cy5.5 and anti-mouse CD19-PE-Cy7 or anti-mouse F4/80 PerCP-Cy5.5, anti-mouse MHCII-PE, anti-mouse CD11b-PE-Cy7 and anti-mouse CD11c-APC FACS antibodies, to classify the cells into various types. The antibodies were purchased from the eBioscience Ltd.

4) In Vitro Toxicity Analysis

The viability of cells was measured using Cell Counting Kit-8 based on aqueous tetrazolium-8 (CCK-8, Dojindo). $5.0 \times 10^3$ HeLa cells in total were seeded on a 96-well plate and treated with different concentrations of 10, 30, 50 or 100 µM of ctCTLA-4 proteins or PBS for 24 hours. After culturing, the cells were washed with PBS and further cultured in the CCK-8 solution for 2 hours. Subsequently, optical density was analyzed using a 450 nm plate reader (Bio-Rad).

5) Isolation of Human PBMC and In Vitro Transfer Efficiency of Respective ctCTLA-4 Proteins The protocol described in relation to the present experiment was approved by the Institutional Review Board (IRB) of Hanyang University. Human blood samples were obtained from healthy donors and blood lymphocytes were isolated by density gradient centrifugation using Ficoll-Paque PLUS (GE Healthcare). The isolated lymphocytes were seeded at $1.0 \times 10^6$ cells/well and transfer efficiency of respective ctCTLA-4 proteins was analyzed. The cells were further stained with anti-human CD4-PE-Cy7, anti-human CD19-APC, anti-human CD11b-PE-Cy7 or anti-human CD11c-APC FACS antibodies, all of which were purchased from eBioscience Ltd.

6) Bio-Imaging of Primary CD4+ T-Cells

The 6 week-old C57BL/6 mice were euthanized, and CD4+ T-cells and lymph nodes were isolated from the spleen using a CD4+ T cell negative selection kit (StemCell Technologies, INC). The isolated CD4+ T-cells in the RPMI medium were seeded on an anti-CD44 antibody-coated glass cover slip equipped in a Chamlide chamber. Then, a protein solution was charged into the chamber and time-lapse imaging was initiated. DIC and GFP images were recorded at an interval of 5 minutes for 2 hours. The obtained time-lapse images were analyzed using MetaMorph or Image J software 1.48v.

7) Transfer Mechanism of Proteins According to the Present Invention

The isolated spleen cells were cultured in the presence of respective ctCTLA-4 proteins at various temperatures (4° C., 25° C. or 37° C.) for one hour. Spleen cells or HeLa cells were pre-treated at 37° C. for 30 minutes with heparin (0, 10, 20 or 50 µg/ml), methyl-beta-cyclodextrin (0, 3, or 5 mM), chlorpromazine (0, 10 or 30 µM) or amiloride (0, 1, 2 or 5 mM) and then treated with respective ctCTLA-4 proteins, and additionally cultured at 37° C. for one hour with respective ctCTLA-4 proteins. All of the cells were treated with trypsin (Thermo Scientific HyClone) and washed with FACS buffer solution (PBS containing 10% FBS, 5% sodium azide and 1% EDTA). Heparin, MβCD, chlorpromazine and amiloride were purchased from Sigma-Aldrich Inc.

8) Bio-Imaging Using Multiphoton Microscope

For in vivo multiphoton imaging of brains, male C57BL/6 mice (23 g-25 g) were subjected to surgical operation to introduce an observation window to the cranium. The animals were narcotized by isoflurane inhalation and kept at a body temperature (37° C.-38° C.) using a homeothermic heating pad system controlled by a rectal probe. The isoflurane level was set to 3% in order to induce narcotization and maintained at 1.5% during the cranium window operation or multiphoton imaging. The animals were monitored in detail throughout the entire process in order to check physiological health of animals. All surgical processes were approved by the Institutional Animal Care and Use Committee (IACUC) of SungKyunKwan University. The animals were fixed on the stereotaxic frame (David Kopf Instruments, Tujunga, Calif.), and a circular cranium window with a diameter of 3 mm was created on the right hemisphere, which was based on ML of +2.5 mm, and AP of −1.5 mm. After craniotomy, a customized chamber plate (Narishige Inc., Tokyo, Japan) having a 5 mm observation hole was placed on an open craniotomy site and immobilized with dentinal resin. Then, the craniotomy window was filled with a sterilized artificial brain spinal cord liquid (125 mM NaCl, 2.5 mM KCl, 25 mM $NaHCO_3$, 1.25 mM $NaH_2PO_4$, 2 mM $CaCl_2$, 1 mM $MgSO_4$, 10 mM glucose, pH 7.4), and covered with a 7 mm cover slip. The craniotomy window was sealed with a cyanoacrylic adhesive agent and the animals were loaded on a head-fixation device (MAG-1, Narishige INC.) for observation using a multiphoton microscope (TCS SP8 MP, Leica Microsystems CMS GmbH). Here, imaging was conducted using a 900 nm Ti:sapphire laser (Chameleon Vision II, Coherent INC.), and emitted fluorescence signals were detected through a 585/40 band-pass filter cube on a hybrid detector (HyD). In order to track transfer of carrier peptides to brain tissues, the carrier peptides were injected in an amount of 2.5 mg/animal through the caudal vein and 3D z-stack images were then obtained at an interval of 20 minutes for 2 hours. The size of imaged brain was $354.29 \times 354.29$ µm$^2$ ($1024 \times 1024$ pixel), which was obtained using a 25× water-immersion objective lens (N.A. 0.95). The imaging depth was about 450 to 500 µm from the brain surface and resolution was 1 µm. After imaging, the corresponding images were analyzed using LAS AF 3.2.0 (Leica Microsystems CMS GmbH) and Imaris 7.7.2 (Bitplane) software.

9) Immunohistochemical Assay 5 mg of each ctCTLA-4 protein was intraperitoneally injected into 6 week-old C57BL/6 mice to analyze the systemic transfer efficiency of dNP2-dTomato. The mice were euthanized 2 hours after injection. Then, the tissues were collected, washed with PBS and immobilized with 4% paraformaldehyde. All of the collected tissues were frozen using an O.C.T. compound (WAKO Chemical). The frozen blocks were cut into sections with a thickness of 6 µm using cryostat (Thermo Scientific) and were inspected by fluorescence microscopy (Leica Microsystems). In order to analyze brain and spinal cord tissues in EAE-induced mice, 2.5 mg of each ctCTLA-4 protein was intravenously injected into the mice, and, after one hour, the animals were euthanized and then transcardially perfused with 15 ml of PBS and then 15 ml of 4% paraformaldehyde. The brain tissues were removed and washed with PBS. Then, the tissues were post-immobilized at room temperature with 4% paraformaldehyde for one hour and protected at a low temperature of 4° C. in 30% sucrose for 24 hours. The brain tissues were frozen using an O.C.T. compound (WAKO Chemical). The frozen blocks were cut into sections with a thickness of 40 µm using a cryostat (Thermo Scientific, Logan, Utah). The sections were cultured in cold acetone at −20° C. for 30 minutes and washed at room temperature with PBS for 30 minutes. The washed samples were cultured in a permeabilization buffer solution (0.5% Triton X-100 in PBS) for 10 minutes and were then cultured in a blocking buffer solution for 20 minutes (3% BSA, 0.1% Tween-20). Primary antibody staining was conducted overnight using anti-mouse CD4-FITC (eBioscience), anti-mouse GFAP (Millipore), anti-mouse Iba-1 (WAKO chemical) or anti-mouse NeuN (Abcam). Nuclei were stained using Hoechst 33342 dye (Invitrogen) or DAPI (Vector Laboratory) after antibody bonding. All section samples were analyzed using a confocal microscope (TCS SP8, Leica Microsystems CMS GmbH).

10) EAE Induction 7-week-old female C57BL/6 mice were purchased from DBL. The protocol described herein was approved by the Institutional Animal Care and Use Committee of Hanyang University. EAE was induced by subcutaneous immunization with 100 μg of MOG35-55 peptide (MEVGWYR-SPFSRVVHLYRNGK) in Freund's adjuvant emulsion (adjuvant-incomplete Freund and 4 mg/ml of Mycobacterium tuberculosis, BD Difco). The total volume of the subcutaneously injected emulsion was 200 μl. 0 hours and 48 hours after immunization, the mice were intra-abdominally treated with 200 ng of pertussis toxin (List Biological Laboratories INC.). Clinical disease symptoms of the animals were scored daily. A dose of each ctCTLA-4 protein diluted in 100 μl of PBS, or fresh PBS alone was intra-abdominally injected. At the end of testing, the mice were euthanized and lymphocytes of the central nervous system were isolated by Percoll density-gradient centrifugation (GE Healthcare). The surfaces of isolated lymphocytes were stained with anti-mouse CD4 PerCP-Cy5.5 antibodies (eBioscience). In addition, the lymphocytes were stained with anti-mouse IFN-γ-FITC and IL-17A-APC antibodies (eBioscience) using a fixation/permeabilization concentration and dilution kit (eBioscience). The cells were analyzed using an FACSCanto flow cytometer and FlowJo software. For histological analysis, paraffin blocks of the spinal cord tissues were de-paraffinized and immersed in Luxol fast blue. For mix staining, hematoxylin & eosin was used (Dako). Invasive cells present in the white area of spinal cord tissues were counted using Image J software 1.48v.

12) In Vivo Toxicity Analysis

PBS and 5 mg/kg of each ctCTLA-4 protein were each repeatedly injected into three groups of C57BL/6 mice every other day for 14 days. Variation in body weight of mice were monitored every day. After 15 days, the mice were sacrificed and the morphologies of the spleen, liver and brain were carefully observed. Cytotoxicity of respective proteins to the spleen cells and thymocytes were analyzed using Annexin V and 7-AAD staining kits (BD bioscience). The percentages of natural CD4 T-cells in the lymph nodes and spleen were analyzed from lymphocytes which had been isolated from the respective tissues, after staining with anti-mouse CD4-PerCP-Cy5.5, anti-mouse CD62L-FITC and anti-mouse CD44-PE FACS antibodies (eBioscience). The hepatotoxicity of proteins was analyzed using an alanine aminotransferase (ALT) activity assay kit (BioVision) and an aspartic acid aminotransferase (AST) activity assay kit (BioVision).

13) Statistics

Data were analyzed using two-tailed Student's t-tests. $p<0.05$ was considered to be significant.

Production Example 1 Synthesis/Separate Purification of Peptides, Fragments Thereof and Fusion Peptides Peptides having amino acid sequences represented by Sequence ID Nos. 1 to 7 were synthesized.

At this time, the peptide having an amino acid sequence represented by Sequence ID No. 1 (hereinafter also referred to as "ctCTLA-4"), the peptide fragment having an amino acid sequence represented by Sequence ID No. 2 (hereinafter also referred to as "ctCTLA-4-fm1"), the peptide fragment having an amino acid sequence represented by Sequence ID No. 3 (hereinafter also referred to as "ctCTLA-4-fm2"), the fusion peptide having an amino acid sequence represented by Sequence ID No. 4 (hereinafter also referred to as "ctCTLA-4-fm3"), the cell-penetrating peptide having an amino acid sequence represented by Sequence ID No. 5 (hereinafter also referred to as "dNP2"), and the cell-penetrating peptide having an amino acid sequence represented by Sequence ID No. 6 (hereinafter also referred to as "Hph-1"), and the cell-penetrating peptide having an amino acid sequence represented by Sequence ID No. 7 (hereinafter also referred to as "TAT") were designated.

Sense and antisense oligodeoxynucleotides suitable for the amino acid sequences were each synthesized and then allowed to stand at 95° C. for 3 minutes to remove the resulting secondary or tertiary structures (denaturation) and DNA double strands were created at different temperatures of 50° C. and then 72° C. In order to insert into pRSET-b vectors, sequences specific to restriction enzymes, apart from the sense and antisense oligodeoxynucleotides, were introduced into 5' and 3'. Then, the sequences were amplified in bulk in *Escherichia*. Then, the integrity of sequences was identified and the sequences were transferred into *Escherichia* to induce expression. Respective peptides expressed from the respective strains were purified.

Production Example 2 Synthesis/Separate Purification of Peptide Variants

Peptides having amino acid sequences represented by Sequence ID Nos. 8 to 10 were synthesized. Peptide variants having Sequence ID Nos. 8 to 10 were obtained by substituting, by F, Y amino acid residues of "1Y" and "2Y" shown in FIG. 1A in the Sequence ID No. 1.

Specifically, the peptide variant having an amino acid sequence represented by Sequence ID No. 8 was obtained by substituting, by F, the Y amino acid residue of the part represented by "1Y", which is represented by "1YF", the peptide variant having an amino acid sequence represented by Sequence ID No. 9 was obtained by substituting, by F, the Y amino acid residue of the part represented by "2Y", which is represented by "2YF", and the peptide variant having an amino acid sequence represented by Sequence ID No. 10 was obtained by substituting, by F, the Y amino acid residues of both "1Y" and "2Y" parts, which is represented by "DYF".

Peptide variants were synthesized and separately purified in the same manner as in Production Example 1 except that the amino acid sequences were used.

Production Example 3 Production of Fusion Products (dNP2-ctCTLA-4, Hph-1-ctCTLA-4, TAT-ctCTLA-4)

In order to fuse the peptide having an amino acid sequence represented by Sequence ID No. 1 produced in Production Example 1 with the cell-penetrating peptide, a primer for linking the cell-penetrating peptide represented by Sequence ID No. 5, Sequence ID No. 6, or Sequence ID No. 7 to the N-end of ctCTLA-4 peptide was produced to produce dNP2-ctCTLA-4, Hph-1-ctCTLA-4 or TAT-ctCTLA-4 genes through PCR reaction, these genes were injected into vectors (pRSET-b) to express proteins in *Escherichia* strains, the proteins were purified, and testing to confirm transfer efficiency of the proteins into cells was conducted. The detailed procedure will be described below.

1) Production of Encoding Genes

The DNA base sequence for encoding the cell-penetrating peptide having an amino acid sequence represented by Sequence ID No. 5, Sequence ID No. 6 or Sequence ID No. 7 was added to the DNA base sequence for encoding a part of the N-end of the peptide having an amino acid sequence represented by Sequence ID No. 1 obtained in Production Example 1 to produce forward primers. Respective primers, Sequence ID Numbers and restriction enzyme recognition sites are briefly shown in Table 1.

PCR reaction was conducted using, as a template, the pRSETb vector containing the gene for encoding the peptide Sequence ID No. 1 with primers represented by the Sequence ID Nos. 18 to 21.

30 cycles were conducted using a PCR reactor (Biorad) and each cycle included initial thermal denaturation reaction at 95° C. for 3 minutes, thermal denaturation reaction of the template at 95° C. for 20 seconds, polymerization reaction for linking the primer to the template at 50° C. for 20 seconds, and elongation reaction at 72° C. for 30 seconds.

TABLE 1

| No. | Primer | Base Sequence |
|---|---|---|
| Seq. ID No. 18 | Primary forward primer of dNP2-ctCTLA-4 | AAGATTAAGAAAGTCAAGAAGA AAGGAAGAAAGGAATTCTACCC ATACGATGTTCCAGATTACGCTA |
| Seq. ID No. 19 | Secondary forward primer of dNP2-ctCTLA-4 | GCTAGCAAGATTAAGAAAGTCA AGAAGAAAGGAAGAAAGGGATC CAAGATTAAGAAAGTCAAGAAGA |
| Seq. ID No. 20 | Forward primer of TAT-ctCTLA-4 | GCTAGCTATGGACGCAAGAAGC GCCGCCAGCGCCGCCGCGGATC CTACCCATACGATGTTCCAGAT TACGCTA |
| Seq. ID No. 21 | Hph-1-ctCTLA-4 primer | TATGCGCGTGTGCGACGTCGTG GCCCACGTCGAGGATCCTACCC ATACGATGTTCCAGATTACGCTA |

Meanwhile, among the forward primers, the dNP2-ctCTLA-4 was divided into two portions for PCR reaction because of very long sequence of dNP2 (KIK-KVKKKGRKGSKIKKVKKKGRK).

2) Production of Recombinant Expression Vectors

In order to express dNP2-ctCTLA-4, Hph-1-ctCTLA-4 or TAT-ctCTLA-4 fusion products, the gene (DNA) fragment produced in 1) of Production Example 3 was cut with a restriction enzyme and then inserted into the protein-expressing vector, pRSETb, using a ligase.

The DNA fragment amplified in 1) of Production Example 3 was subjected to enzyme reaction using NheI and HindIII (NEB) such that the 5'/3' ends of the DNA became sticky ends. Meanwhile, pRSETb was subjected to enzyme reaction using two identical restriction enzymes to produce linear pRSETb vectors having NheI and HindIII insertion sites. After respective enzyme reactions, isolation was conducted using a PCR purification kit (Cosmogenetech Co., Ltd.).

The isolated dNP2-ctCTLA-4, Hph-1-ctCTLA-4 or TAT-ctCTLA-4 fusion product double-chain DNA fragments were connected to the pRSET-b vectors at 25° C. for two hours by enzyme reaction using a T4 ligase (NEB). The connected circular pRSETb vectors into which dNP2-ctCTLA-4, Hph-1-ctCTLA-4 or TAT-ctCTLA-4 thus was inserted were transformed into DH5α *Escherichia* strains and cultured in LB plate medium containing 50 μg/ml of ampicillin as an antibiotic to select transformed *Escherichia* for forming colonies. The selected *Escherichia* colonies were cultured in a liquid medium (LB) containing 50 μg/ml of ampicillin again and plasmid vectors were then isolated using a plasmid mini preparation kit (Cosmogenetech Co., Ltd.).

In order to identify that the plasmid vector isolated through the process was the pRSETb vector into which the dNP2-ctCTLA-4, Hph-1-ctCTLA-4 or TAT-ctCTLA-4 was inserted, enzyme reaction was primarily conducted using NheI and HindIII restriction enzymes and DNA base sequence analysis (bionics) was then finally conducted.

3) Isolation and Purification of Proteins

The pRSETb vector, into which dNP2-ctCTLA-4, Hph-1-ctCTLA-4, TAT-ctCTLA-4 or dNP2-ctCTLA-4-fm3 was inserted, produced in 2) of the Production Example 3, was transformed into *Escherichia* BL21 (DE3) Star pLysS strains, colonies created in a LB plate medium containing 34 μg/ml of chloramphenicol and 50 μg/ml of ampicillin as antibiotics were seeded into 50 ml of a liquid LB medium and cultured at 37° C. for 10 hours, and the resulting culture solution was seeded into 500 mL of a fresh LB liquid medium. The solution was cultured until the amount of *Escherichia* corresponded to O.D. of 0.5 when the culture solution was measured at the same temperature, isopropyl β-D-1-thiogalactopyranoside (IPTG) was added at a concentration of 1 mM and further cultured in a shaking incubator having a temperature of 20° C. and at a constant rotation rate of 150 rpm for 14 hours. The proteins expressing *Escherichia* strains included a 6X-His tag encoded in pRSET-b vectors at a front side thereof. The proteins were purified using this by the following testing method.

Figure 2:
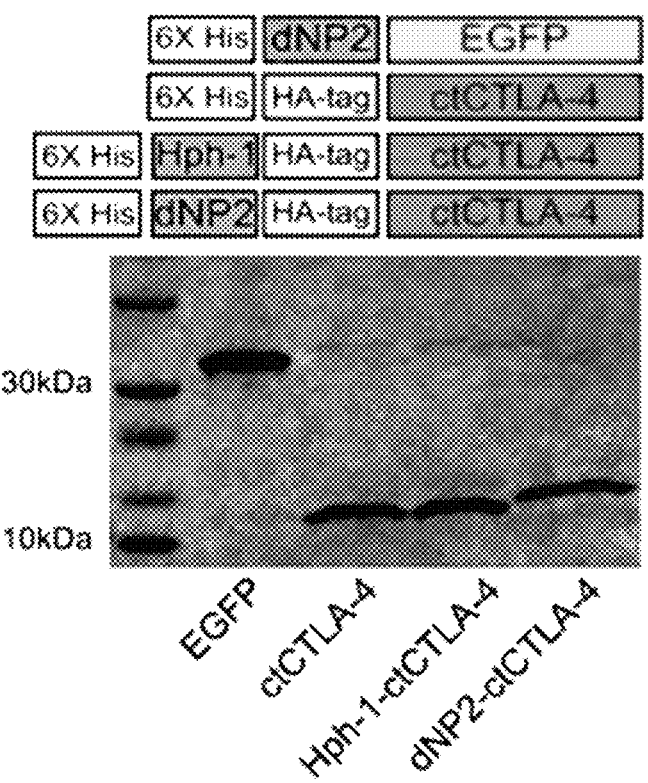
FIG. 2 shows the structure of a dNP2-ctCTLA-4 fusion protein according to the present invention and analysis results of the dNP2-ctCTLA-4 fusion protein using SDS-PAGE.

The culture solution was collected by centrifugation and then re-suspended in a native lysis solution (0.5M NaCl, 5 mM imidazole, 20 mM Tris-HCl, pH 8.0). In order to disrupt *Escherichia* cell walls and cell membranes, the suspension in the lysis solution was allowed to stand for 10 minutes. In addition, the cells were broken using an ultrasonic cell disrupter VCX-130 (Sonics & Materials) and centrifuged to isolate the supernatant. The isolated supernatant was filtered once using a 0.45 μm filter (Advantec) and then bonded to Ni-NTA agarose (Qiagen) at room temperature for 1 hour. Then, only the Ni-NTA agarose-bonded protein product was bound to the column using a histidine column (His-column, Biorad). The column was washed with 20 mM and 250 mM imidazole solutions and finally eluted using a 3M imidazole solution. The eluted protein product was applied to a PD-10 desalting column (Amersham Bioscience) to finally purely isolate and purify the dNP2-ctCTLA-4, Hph-1-ctCTLA-4 or TAT-ctCTLA-4 fusion product. A part of the purified protein was identified through 12% SDS-PAGE and is shown in FIG. 2.

Production Example 4 Production of dNP2-ctCTLA-4-fm3 Fusion Product

The fusion product (hereinafter, also referred to as "dNP2-ctCTLA-4-fm3 fusion product") including the fusion peptide (hereinafter, also referred to as "ctCTLA-4-fm3") having an amino acid sequence represented by Sequence ID No. 4, produced in Production Example 1, and the cell-penetrating peptide (dNP2) having an amino acid sequence represented by Sequence ID No. 5 was synthesized by Cosmogenetech Co., Ltd.

Production Example 5 Synthesis and Separate Purification of Control Group (dNP2-EGFP)

In order to fuse the cell-penetrating peptide having an amino acid sequence represented by Sequence ID No. 5 produced in Production Example 1 with a green florescent protein (EGFP), primers for binding EGFP to the N-end of dNP2 were produced, dNP2-EGFP genes were produced through PCR reaction and inserted into vectors (pRSET-b), and proteins were expressed in *Escherichia* strains and purified. The overall process was the same as in Production Example 3, except for the primers. The primers used are as follows.

```
Primary forward primer
                             [Sequence ID No. 22]
AAGATTAAGAAAGTCAAGAAGAAAGGAAGAAAGGTGAGCAAGGGCGAGGA
GCTGTTCACCG Secondary forward primer
                             [Sequence ID No. 23]
GCTAGCAAGATTAAGAAAGTCAAGAAGAAAGGAAGAAAGGGATCCAAGAT
TAAGAAAGTCAAGAAGA
```

Production Example 6 Synthesis of Control Group (dNP2-TAMRA)

In order to produce a fusion product of the cell-penetrating peptide having an amino acid sequence represented by Sequence ID No. 5 produced in Production Example 1 with a florescent labelling compound, TARMA, the substance synthesized by Cosmogenetech Co., Ltd. was used.

Test Example 1

1) Transfer Efficiencies of ctCTLA-4 Peptide, and dNP2-ctCTLA-4 and Hph-1-ctCTLA-4 Fusion Products into Mouse Spleen Cells (Immune Cells)

The intracellular introduction efficiency was compared between the ctCTLA-4 peptide purified in Production Example 1, and dNP2-ctCTLA-4 and Hph-1-ctCTLA-4 fusion products purified in Production Example 3.

Specifically, the transfer efficiency was measured using "3) In vitro transfer efficiency" in the test method, which will be briefly described below.

Mouse spleen cells were cultured together with 1 µM of a ctCTLA-4 peptide, or a dNP2-ctCTLA-4 or Hph-1-ctCTLA-4 fusion product for one hour, and the ctCTLA-4 peptide or CPP-linked ctCTLA-4 fusion products, which had been transferred into cells, were stained with anti-HA antibodies. Signals were amplified with PE-conjugated anti-rabbit IgG antibodies. The cells were harvested and intracellular fluorescence was measured using a flow cytometer to measure ctCTLA-4 protein introduction efficiency in primary mouse CD4-T-cells.

Figure 3:
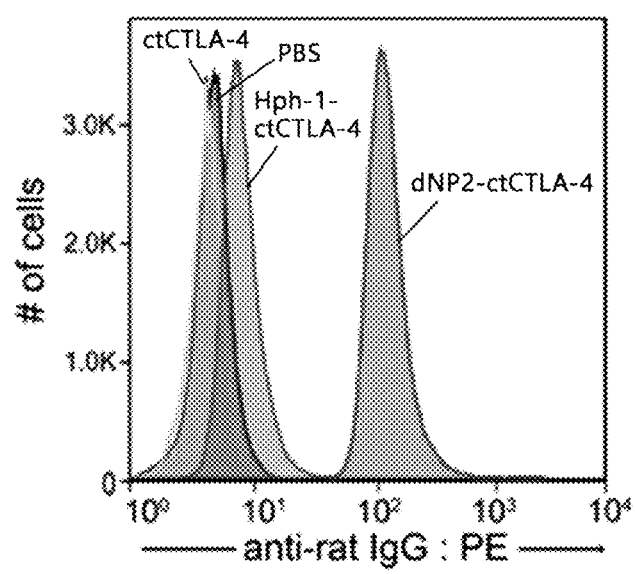
FIG. 3 is a graph showing intracellular transfer efficiencies of a ctCTLA-4 peptide, and dNP2-ctCTLA-4 and Hph-1-ctCTLA-4 fusion products in primary mouse CD4 T-cells.

FIG. 3 is a graph showing intracellular transfer efficiencies of the ctCTLA-4 peptide, and dNP2-ctCTLA-4 and Hph-1-ctCTLA-4 fusion products in primary mouse CD4-T-cells.

As shown in FIG. 3, 1 µM of the ctCTLA-4 peptide exhibited excellent intracellular transfer efficiency even though it was not linked to the cell-penetrating peptide (hereinafter, also referred to as "CPP").

It could be seen that, when the CPP was linked to the ctCTLA-4 peptide, intracellular transfer efficiency of (dNP2-ctCTLA-4 or Hph-1-ctCTLA-4 fusion product) was further improved, preferably, the dNP2-ctCTLA-4 fusion product exhibited the highest intracellular transfer efficiency. Specifically, the dNP2-ctCTLA-4 fusion product exhibited about at least 10 times higher intracellular transfer efficiency than the Hph-1-ctCTLA-4 fusion product and the ctCTLA-4 peptide.

Through the test, the dNP2-ctCTLA-4 fusion product having the most excellent transfer efficiency was screened from the fusion products wherein CPP was fused to ctCTLA-4, and in the following test, comparison and analysis were conducted based on the dNP2-ctCTLA-4 fusion product produced using dNP2, which is representative of conventional CPPs.

Test Example 2

Figure 17:
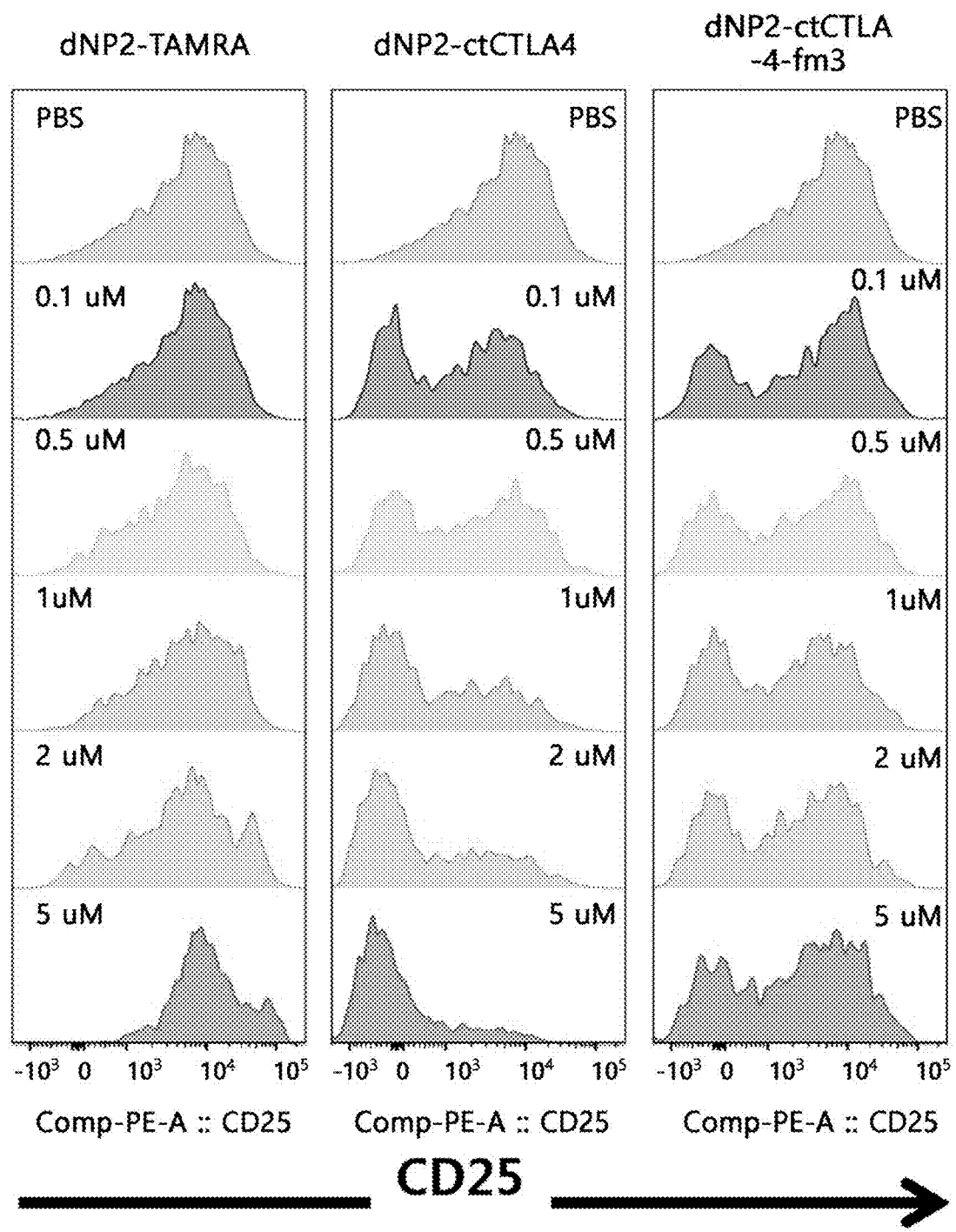
FIG. 17 is a graph showing intracellular transfer efficiencies of 0.1, 0.5, 1, 2 or 5 µM dNP2-TAMRA fusion product, dNP2-ctCTLA-4 fusion product and dNP2-ctCTLA-4-fm3 fusion product in primary mouse CD4-T-cells.

1) Evaluation of IL-2 Expression Inhibitory Ability of CPP-ctCTLA-4 Fusion Product Depending on Type of CPP The spleen cells activated by anti-CD3 and anti-CD28 antibodies were treated with 1 µM of each of PBS, the dNP2-ctCTLA-4 fusion product and the TAT-ctCTLA-4 fusion product, and IL-2 expression inhibitory efficiency was measured by ELISA and shown in FIG. 17.

First, a 96-well plate was coated at a concentration of 0.1 µg/well with anti-CD3 (anti-mouse CD3) and anti-CD28 (anti-mouse CD28) monoclonal antibodies at 37° C. for 5 hours, spleen cells were isolated from 7-week-old C57BL/6, and the isolated spleen cells were suspended to be single cells. The spleen cells suspended through the process were seeded at $2.5 \times 10^5$ on each well coated with anti-CD3 (anti-mouse CD3) and anti-28 (anti-mouse CD28) monoclonal antibodies, and were treated with 1 µM PBS, the dNP2-ctCTLA-4 fusion product and the TAT-ctCTLA-4 fusion product, and then activated for 24 hours.

Figure 4:
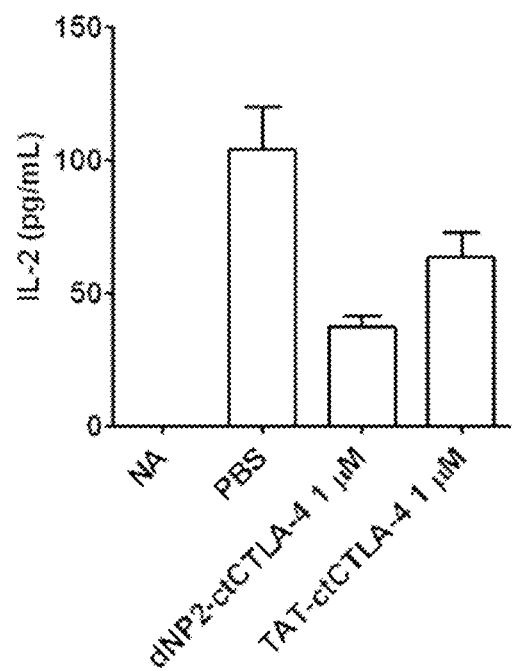
FIG. 4 is a graph showing IL-2 expression inhibitory efficiency of 1 µM PBS, dNP2-ctCTLA-4 fusion product and TAT-ctCTLA-4 fusion product. The numbers represent mean±s.e.m., and * represents $p<0.05$,  represents $p<0.01$, and * represents $p<0.001$; Student's t-test.

FIG. 4 is a graph showing IL-2 expression inhibitory efficiency of 1 µM PBS, the dNP2-ctCTLA-4 fusion product and the TAT-ctCTLA-4 fusion product. The numbers represent mean±s.e.m., and * represents p<0.05,  represents p<0.01, and * represents p<0.001; Student's t-test.

As can be seen from FIG. 4, the ctCTLA-4 protein according to the present invention exhibited a 40% to 70% decrease in IL-2 expression through linkage with the conventional cell-penetrating peptide (TAT, dNP2, Hph-1), compared to the counterpart subjected to PBS treatment.

It could be seen that, among them, the dNP2-ctCTLA-4 fusion product exhibited the best decrease effect of 70% (specifically, at least two times higher effect than the TAT-ctCTLA-4 fusion product).

2) Evaluation of IL-2 Expression Inhibitory Ability of ctCTLA-4

IL-2 expression inhibitory ability was compared between the dNP2-ctCTLA-4 fusion product purified in Production Example 3 and the dNP2-EGFP fusion product (Control group) purified in Production Example 5.

The spleen cells activated by the anti-CD3 and anti-CD28 antibodies were each treated with the dNP2-ctCTLA-4 fusion product and the dNP2-EGFP fusion product, and IL-2 expression inhibitory efficiency was measured by ELISA and shown in FIG. 4A. At this time, ELISA was conducted using the kit produced by Biolegend Corporation in accordance with the standard protocol provided by the manufacturer.

In addition, spleen cells activated by PMA/ionomycin were treated with the dNP2-ctCTLA-4 fusion product and the dNP2-EGFP fusion product, and IL-2 expression inhibitory efficiency was measured by ELISA and is shown in FIG. 4B.

At this time, the activated spleen cells were activated with the anti-CD3/CD28 antibody or PMA/ionomycin in the presence of 1 µM PBS, the dNP2-ctCTLA-4 fusion product or dNP2-EGFP fusion product for 24 hours.

FIGS. 5A and 5B are graphs showing IL-2 expression inhibitory efficiency of the dNP2-ctCTLA-4 fusion product and the dNP2-EGFP fusion product. The numbers represent mean±s.e.m., and * represents $p<0.05$,  represents $p<0.01$, and * represents $p<0.001$; Student's t-test.

Figure 5:
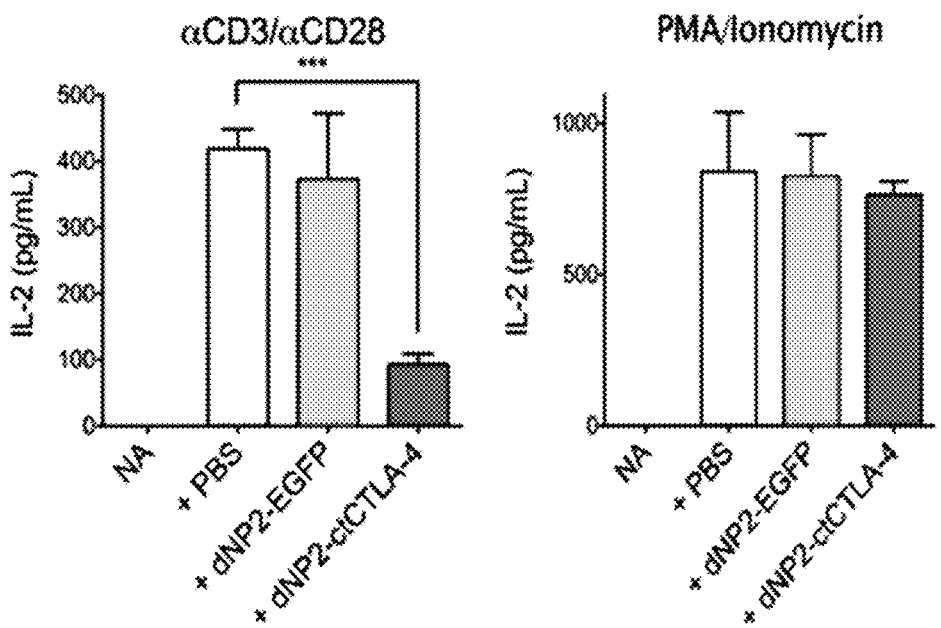
FIGS. 5A and 5B are graphs showing IL-2 expression inhibitory efficiency of the dNP2-ctCTLA-4 fusion product and the dNP2-EGFP fusion product. The numbers represent mean±s.e.m., and * represents $p<0.05$,  represents $p<0.01$, and * represents $p<0.001$; Student's t-test.

As can be seen from FIG. 5, the dNP2-ctCTLA-4 fusion product inhibited IL-2 expression, while the dNP2-EGFP fusion product could not inhibit IL-2 expression.

Furthermore, the dNP2-ctCTLA-4 fusion product according to the present invention did not have any effect on the spleen cells activated by stimulation of PMA and ionomycin, which demonstrates that the target of the dNP2-ctCTLA-4 fusion product was adjacent TcR signal molecules. That is, the dNP2-ctCTLA-4 fusion product according to the present invention had a specific-target directivity.

In addition, the IL-2 expression inhibitory effect was due to ctCTLA-4, not dNP2.

3) Evaluation of IFN-γ and IL-17A Expression Inhibitory Ability of ctCTLA-4

IFN-γ and IL-17A expression inhibitory abilities were compared between the dNP2-ctCTLA-4 fusion product purified in Production Example 3 and the dNP2-EGFP fusion product (Control group) purified in Production Example 5.

The spleen cells activated by the anti-CD3 and anti-CD28 antibodies were each treated with the dNP2-ctCTLA-4 fusion product and the dNP2-EGFP fusion product, and IFN-γ and IL-17A expression inhibitory abilities were measured by ELISA and are shown in FIG. 6.

Figure 6A:
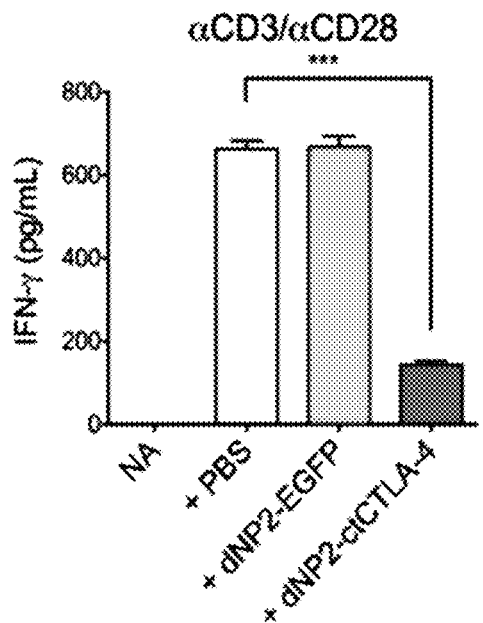
FIG. 6A is a graph showing IFN-γ expression inhibitory efficiency of the dNP2-ctCTLA-4 fusion product and the dNP2-EGFP fusion product and FIG. 6B is a graph showing IL-17A expression inhibitory efficiency of the dNP2-ctCTLA-4 fusion product and the dNP2-EGFP fusion product. The numbers represent mean±s.e.m., and * represents $p<0.05$,  represents $p<0.01$, and * represents $p<0.001$; Student's t-test.
Figure 6B:
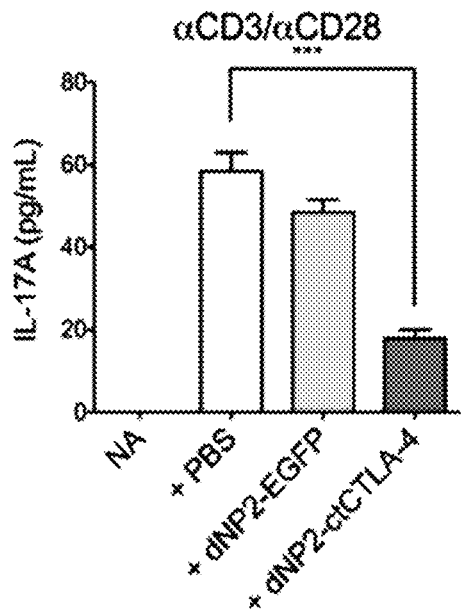

FIG. 6A is a graph showing IFN-γ expression inhibitory efficiency of the dNP2-ctCTLA-4 fusion product and the dNP2-EGFP fusion product and FIG. 6B is a graph showing IL-17A expression inhibitory efficiency of the dNP2-ctCTLA-4 fusion product and the dNP2-EGFP fusion product. The numbers represent mean±s.e.m., and * represents $p<0.05$,  represents $p<0.01$, and * represents $p<0.001$; Student's t-test.

As can be seen from FIG. 6, levels of interferon-γ (IFN-γ) and interleukin-17A (IL-17A) expressed in activated spleen cells were significantly decreased by the dNP2-ctCTLA-4 fusion product. Specifically, the dNP2-ctCTLA-4 fusion product according to the present invention had at least 3 times lower expression level than the dNP2-EGFP fusion product.

Test Example 3

1) Preventive Effect of ctCTLA-4 in Multiple Sclerosis Mouse Model (EAE-Induced Animal Model)

In order to analyze inhibitory effect of ctCTLA-4 in the multiple sclerosis mouse model, the present invention adopted, as a standard EAE model, C57BL/6 mice immunized by $MOG_{35-55}$ peptide and treated with pertussis toxin.

At this time, as described above, the EAE was induced in 7-week-old C57BL/6 mice. 7 days after MOG immunization, the mice were treated with PBS, 25 βg of dNP2-ctCTLA-4 fusion product or dNP2-EGFP fusion product by intra-abdominal injection, and then treated every other day (preventive scheme, n=15). After induction of EAE in the mice, the mice were observed every day and scores of EAE clinical symptoms are shown in FIG. 7.

Figure 7:
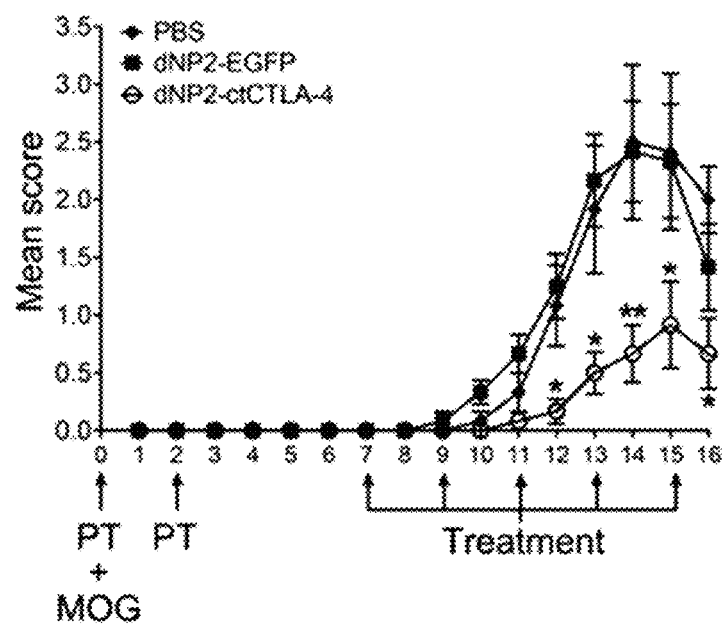
FIG. 7 is a graph showing test results of 1) of Test Example 3 and this graph shows clinical scores in the EAE animal model as a function of day (y axis) after disease induction in respective groups (x axis). The numbers represent mean±s.e.m., and * represents $p<0.05$,  represents $p<0.01$ and * represents $p<0.001$; Student's t-test.

FIG. 7 is a graph showing test results of 1) of Test Example 3 and this graph shows clinical scores in the EAE animal model as a function of day (y axis) after disease induction in respective groups (x axis). The numbers represent mean±s.e.m., and * represents $p<0.05$,  represents $p<0.01$ and * represents $p<0.001$; Student's t-test.

The EAE clinical symptoms were evaluated by scoring based on the grades shown in Table 2.

TABLE 2

| Score | Description |
| --- | --- |
| 0 | Normal behavior: no neurological symptoms |
| 0.5 | Paralyzed, unable to roll tail |
| 1 | Unable to move tail |
| 2 | Limping: unstable back leg during walking |
| 2.5 | One back leg completely-paralyzed |
| 3 | Two back legs completely-paralyzed: difficult to stand with back legs, but still possible to move the remaining legs |
| 3.5 | Unable to normally move even front legs |
| 4 | All legs of mice are paralyzed and cannot move, and mice became thin and gaunt |
| 5 | Death |

As can be seen from FIG. 7, the clinical score of mice treated with the dNP2-ctCTLA-4 fusion product was kept low, rather than being significantly increased, compared to the clinical score of mice treated with the dNP2-EGFP fusion product or PBS.

On the other hand, the mice treated with the dNP2-EGFP fusion product or PBS started to show clinical symptoms at 9 days and then their conditions very rapidly worsened, that is, all back legs were paralyzed or in serious cases, all limbs were paralyzed. However, mice treated with the dNP2-ctCTLA-4 fusion product started to show clinical symptoms at 11 days and then their conditions very slowly worsened and, even in the most serious case, only the tail was paralyzed. These results showed that the dNP2-ctCTLA-4 fusion product according to the present invention was highly effective in preventing central nervous system diseases, in particular, multiple sclerosis.

2) Preventive Effect of CPP-ctCTLA-4 Fusion Product Depending on Type of CPP in Multiple Sclerosis Mouse Model (EAE-Induced Animal Model)

In order to analyze inhibitory effect of the ctCTLA-4 fusion product depending on type of CPP in the multiple sclerosis mouse model, the present invention adopted, as a standard EAE model, C57BL/6 mice immunized by $MOG_{35-55}$ peptide and treated with pertussis toxin.

At this time, as described above, the EAE was induced in 7-week-old C57BL/6 mice. 7 days after MOG immunization, the mice were each treated with PBS, 25 μg of the dNP2-ctCTLA-4 fusion product and the Hph-1-ctCTLA-4 fusion product by intra-abdominal injection, and then treated with the same every other day (preventive scheme, n=15). After induction of EAE in the mice, the mice were observed every day and scores of EAE clinical symptoms are shown in FIG. 8.

Figure 8:
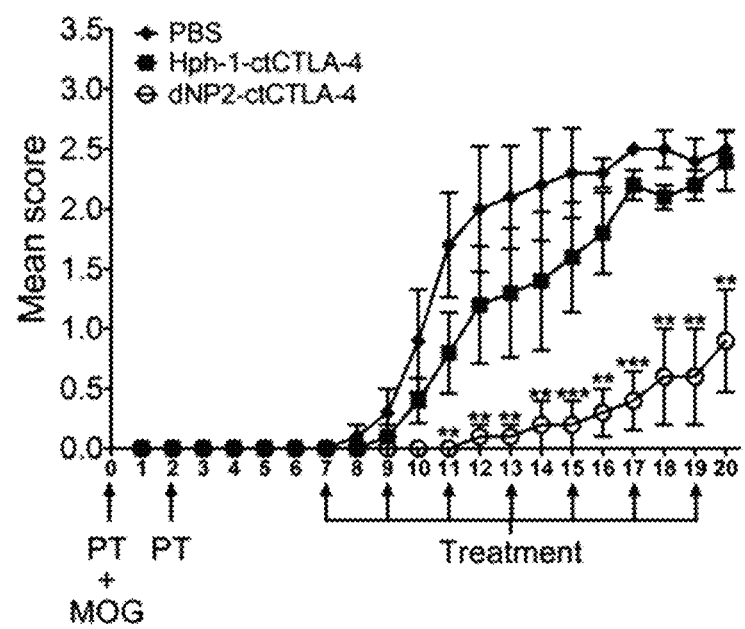
FIG. 8 is a graph showing test results of 2) of Test Example 3 and this graph shows clinical scores in the EAE animal model as a function of day (y axis) after disease induction in respective groups (x axis). The numbers represent mean±s.e.m., and * represents $p<0.05$,  represents $p<0.01$, and * represents $p<0.001$; Student's t-test.

FIG. 8 is a graph showing test results of 2) of Test Example 3 and this graph shows clinical scores on the EAE animal model as a function of day (y axis) after disease induction in respective groups (x axis). The numbers represent mean±s.e.m., and * represents $p<0.05$,  represents $p<0.01$, and * represents $p<0.001$; Student's t-test.

The EAE clinical symptoms were evaluated by scoring based on the grades shown in Table 2.

As can be seen from FIG. 8, the mice treated with the Hph-1-ctCTLA-4 fusion product started to show clinical symptoms at 9 days which was slightly later and more slowly worsened, compared to the mice treated with only PBS. That is, the Hph-1-ctCTLA-4 fusion product also exhibited excellent penetration ability to blood-brain barriers or blood-spinal cord barriers as well as segmentation of in vivo brain tissues, and had effects of preventing or relieving substantially central nervous system diseases, in particular, multiple sclerosis.

However, the mice treated with the dNP2-ctCTLA-4 fusion product started to show clinical symptoms at 11 days and their conditions then very slowly worsened and even in the most serious case, only the tail was paralyzed. These results showed that the dNP2-ctCTLA-4 fusion product according to the present invention has the best effect of preventing central nervous system diseases, in particular, multiple sclerosis.

3) Preventive Effect of ctCTLA-4 Depending on Dose in Multiple Sclerosis Mouse Model (EAE-Induced Animal Model)

In order to analyze the inhibitory effect of ctCTLA-4 depending on dose of ctCTLA-4 in the multiple sclerosis mouse model, the present invention adopted, as a standard EAE model, C57BL/6 mice immunized by $MOG_{35-55}$ peptide and treated with pertussis toxin.

At this time, as described above, the EAE was induced in 7-week-old C57BL/6 mice. 7 days after MOG immunization, the mice were each treated with PBS, 100 μg of the dNP2-ctCTLA-4 fusion product and the dNP2-EGFP fusion product by intra-abdominal injection, and then treated with the same every other day (preventive scheme, n=15). After induction of EAE in the mice, the mice were observed every day and scores of EAE clinical symptoms are shown in FIG. 9.

Figure 9:
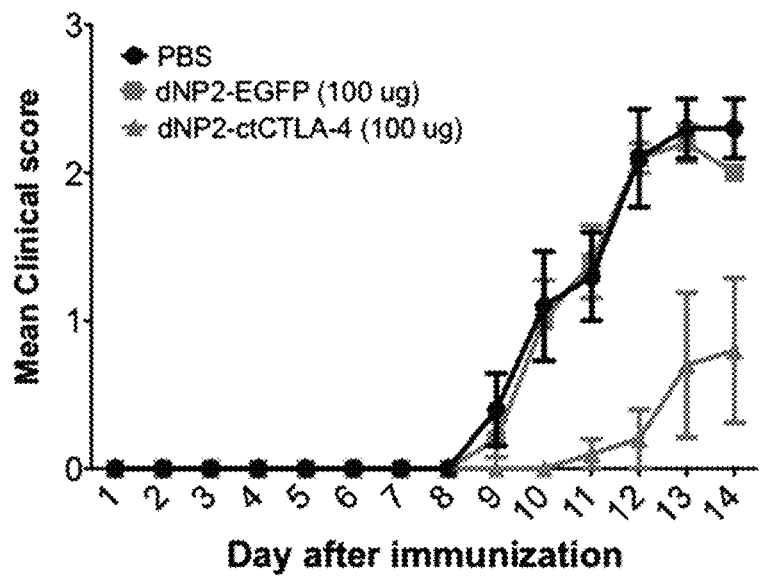
FIG. 9 is a graph showing test results of 3) of Test Example 3 and this graph shows clinical scores in the EAE animal model as a function of day (y axis) after disease induction in respective groups (x axis). The numbers represent mean±s.e.m., and * represents $p<0.05$,  represents $p<0.01$, and * represents $p<0.001$; Student's t-test.

FIG. 9 is a graph showing test results of 3) of Test Example 3 and this graph shows clinical scores in the EAE animal model as a function of day (y axis) after disease induction in respective groups (x axis). The numbers represent mean±s.e.m., and * represents $p<0.05$,  represents $p<0.01$, and * represents $p<0.001$; Student's t-test.

The EAE clinical symptoms were evaluated by scoring based on the grades shown in Table 2.

As can be seen from FIG. 9, the clinical score of mice treated with the dNP2-ctCTLA-4 fusion product was significantly lower than that of mice treated with the dNP2-EGFP fusion product or PBS.

That is, it can be seen that the results shown in FIG. 9 are very similar to those shown in FIG. 7 with only a different dose. This indicates that the dose of the fusion product has no great effect on clinical score in the animal model.

4) Therapeutic Effect of ctCTLA-4 in Multiple Sclerosis Mouse Model (EAE-Induced Animal Model)

100 μg of the dNP2-ctCTLA-4 fusion product or dNP2-EGFP fusion product was intra-abdominally injected into the animal model wherein a disease developed and had an average clinical score of 1, to confirm therapeutic effects.

In the present Test Example, C57BL/6 mice immunized by $MOG_{35-55}$ peptide and treated with pertussis toxin were used as a standard EAE model. As described above, the EAE was induced in 7-week-old C57BL/6 mice. After MOG immunization, the mice were allowed to stand until the average clinical score reached 1 (on 10 days) and were each treated with PBS, 100 μg of the dNP2-ctCTLA-4 fusion product and 100 μg of the dNP2-EGFP fusion product by intra-abdominal injection, then treated again with the same at 12 days, every other day and then treated every day (preventive scheme, day 10, n=5). After induction of EAE in the mice, the mice were observed every day and scores of EAE clinical symptoms are shown in FIG. 10.

Figure 10:
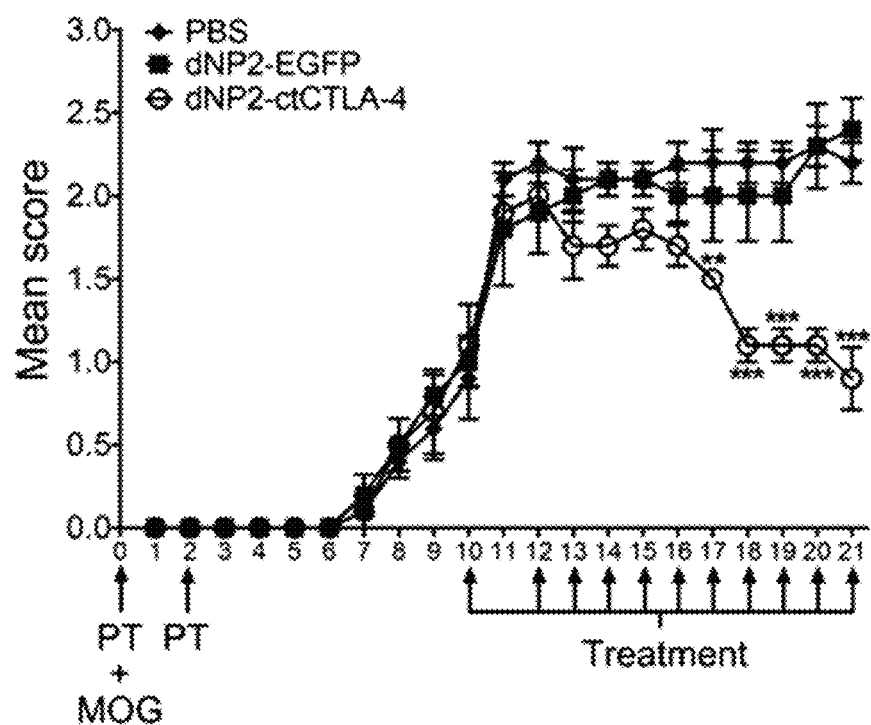
FIG. 10 is a graph showing test results of 4) of Test Example 3 and this graph shows clinical scores in the EAE animal model as a function of day (y axis) after disease induction in respective groups (x axis). The numbers represent mean±s.e.m., and * represents $p<0.05$,  represents $p<0.01$, and * represents $p<0.001$; Student's t-test.

FIG. 10 is a graph showing test results of 4) of Test Example 3 and this graph shows clinical scores in the EAE animal model as a function of day (y axis) after disease induction in respective groups (x axis). The numbers represent mean±s.e.m., and * represents $p<0.05$,  represents $p<0.01$, and * represents $p<0.001$; Student's t-test.

The EAE clinical symptoms were evaluated by scoring based on the grades shown in Table 2.

As can be seen from FIG. 10, the mice that had symptoms developed to a clinical score of 2.0 could be recovered to the clinical score of 1.0 by treating with the dNP2-ctCTLA-4 fusion product.

In other words, from the data according to the present invention, it could be concluded that the dNP2-ctCTLA-4 fusion product could be used as an immune-regulatory protein that is capable of regulating activated T-cell reaction in vitro and in vivo as well as central nervous system diseases such as multiple sclerosis (requiring penetration of the blood-brain barrier and the blood-spinal cord barrier).

On the other hand, treatment with the dNP2-EGFP fusion product led to maintenance or increase of the clinical score to 2.5 or more (that is, symptoms worsened), rather than decrease in clinical score.

5) Demyelination of ctCTLA-4 and Invasion Inhibitory Effects of Immune Cells in Multiple Sclerosis Mouse Model (EAE-Induced Animal Model)

Figure 11:
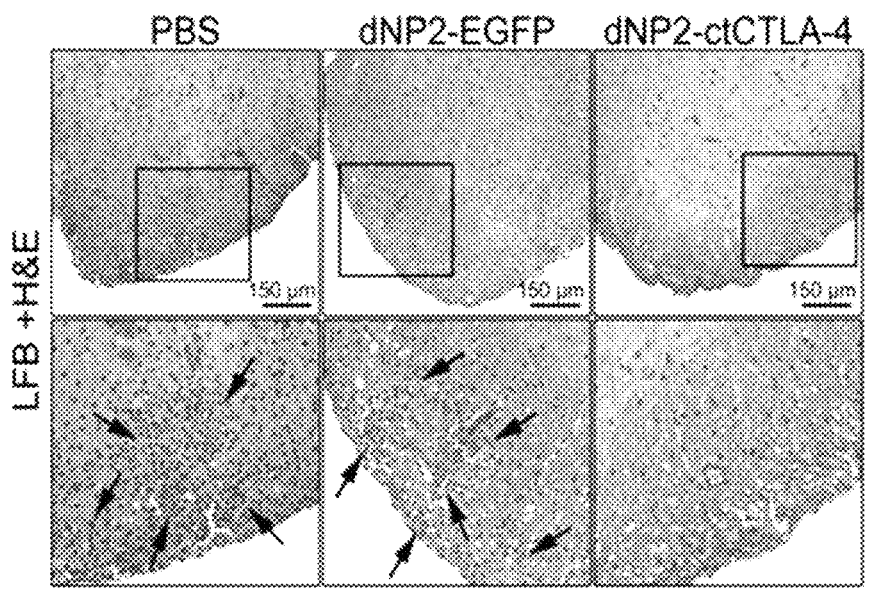
FIG. 11 is images of luxol fast blue (LFB) and hematoxylin & eosin (H&E) staining showing the effects of the dNP2-ctCTLA-4 fusion product and the dNP2-EGFP fusion product according to the present invention on demyelination and invasion of immune cells in the EAE-induced animal model, wherein the scale bar is 100 µm.

FIG. 11 is images of luxol fast blue (LFB) and hematoxylin & eosin (H&E) staining showing the effects of the dNP2-ctCTLA-4 fusion product and the dNP2-EGFP fusion product according to the present invention on demyelination and invasion of immune cells in the EAE-induced animal model. The scale bar was 100 μm.

Figure 12:
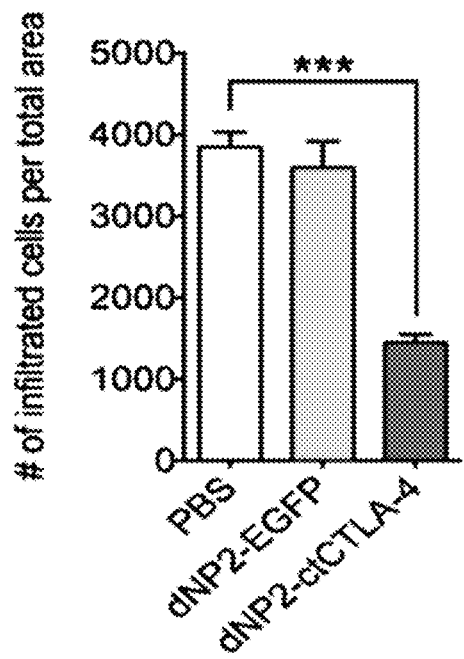
FIG. 12 is a graph showing the numbers of invasive immune cells of spinal cord tissues according to respective treatment groups measured in FIG. 11, wherein the numbers are counted using Image J software 1.48v. The numbers represent mean±s.e.m., and * represents $p<0.05$,  represents $p<0.01$, and * represents $p<0.001$; Student's t-test.

FIG. 12 is a graph showing the numbers of invasive immune cells of spinal cord tissues according to respective treatment groups measured in FIG. 11, wherein the numbers are counted using Image J software 1.48v. The numbers represent mean±s.e.m., and * represents p<0.05,  represents p<0.01, and * represents p<0.001; Student's t-test.

As shown in FIGS. 11 and 12, results of testing inhibitory effects of the dNP2-ctCTLA-4 fusion product and the dNP2-EGFP fusion product on demyelination and invasion of immune cells in the EAE animal model found that the animal model treated with the dNP2-ctCTLA-4 fusion product showed decreases in demyelination and invasion of immune cells, compared to in other animal cells. This indicates that inflammation of spinal cord tissues was significantly decreased in the mouse model treated with the dNP2-ctCTLA-4 fusion product.

6) Flow Cytometry of ctCTLA-4 in Multiple Sclerosis Mouse Model (EAE-Induced Animal Model)

Figure 13:
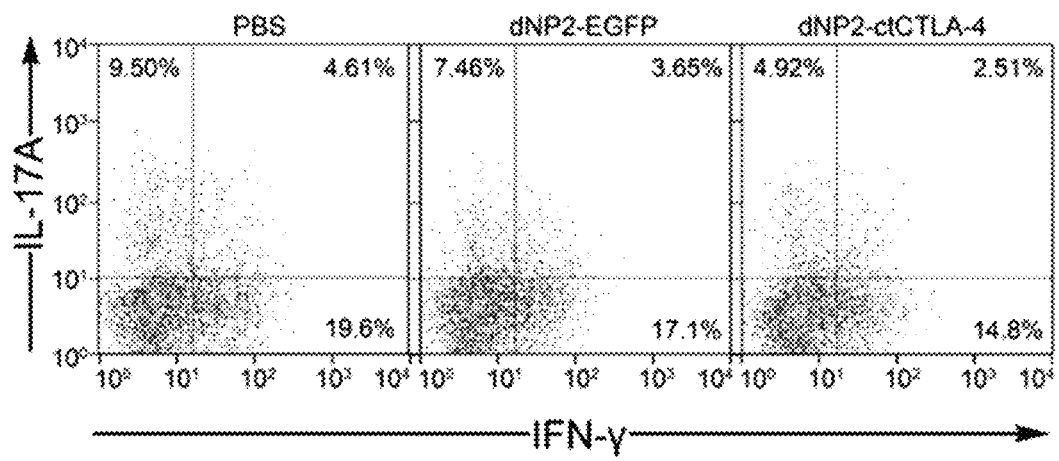
FIG. 13 shows results of flow cytometry of IL-17A and/or IFN-γ expression CD4 T-cells after isolation of spinal cord cells in EAE animal models treated with Th1, Th17, Th2 and Treg cells (T-cells), regarding the dNP2-ctCTLA-4 fusion product and dNP2-EGFP fusion product according to the present invention.
Figure 14A:
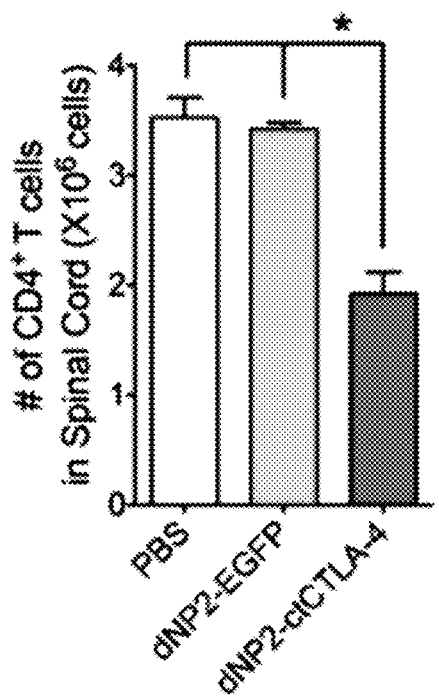
FIG. 14 is a graph showing analysis of results of FIG. 13. The absolute cell numbers are counted in a fraction in which a single cell from the spinal cord is suspended. By multiplying the numbers, the ratios of CD4+ cells (a), IFNγ+ CD4+ cells (b), IL-17A+CD4+ cells (c) and IFNγ+IL-17A+ CD4+ cells (d) in total are measured and data are shown as a bar graph (n=15). The numbers represent mean±s.e.m., and * represents $p<0.05$,  represents $p<0.01$, and * represents $p<0.001$.
Figure 14B:
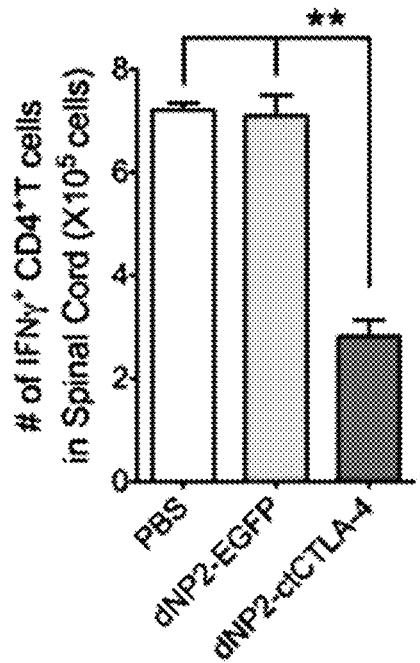
Figure 14C:
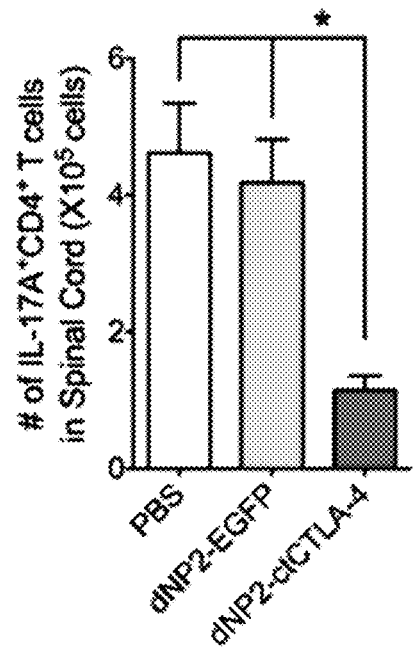
Figure 14D:
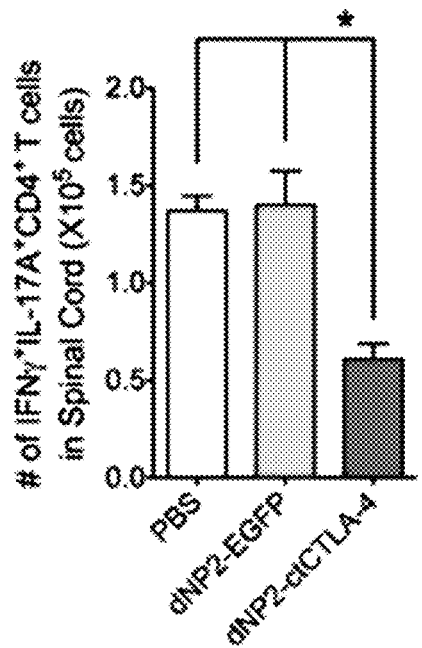

FIG. 13 shows results of flow cytometry of IL-17A and/or IFN-γ expression CD4 T-cells after isolation of spinal cord cells in EAE animal models treated with Th1, Th17, Th2 and Treg cells (T-cells) of the dNP2-ctCTLA-4 fusion product and the dNP2-EGFP fusion product according to the present invention.

FIG. 14 is a graph showing analysis of results of FIG. 13. The absolute cell numbers were counted in a fraction in which a single cell from the spinal cord was suspended. By multiplying the numbers, the ratios of CD4+ cells (a), IFNγ+CD4+ cells (b), IL-17A+CD4+ cells (c) and IFNγ+IL-17A+CD4+ cells (d) in total were measured and data are shown as a bar graph (n=15). The numbers represent mean±s.e.m., and * represents p<0.05,  represents p<0.01, and * represents p<0.001; Student's t-test.

As shown in FIGS. 13 and 14, the proportion and number of invaded IFN-γ- and/or IL-17A-producing CD4 T-cells in the spinal cord tissues were significantly decreased only when treated with the dNP2-ctCTLA-4 fusion product.

Test Example 4

Evaluation of Performance of Fragment Peptides Represented by Sequence ID Nos. 2 and 3, and Fusion Peptide Represented by Sequence ID No. 4

1) Evaluation of IL-2 Expression Inhibitory Ability of ctCTLA-4 Peptides and Variants Thereof IL-2 expression inhibitory abilities were compared between the ctCTLA-4 peptide purified in Production Example 1 (represented by "WT" in the present Test Example) and 1YF, 2YF or DYF variants purified in Production Example 2.

Figure 15:
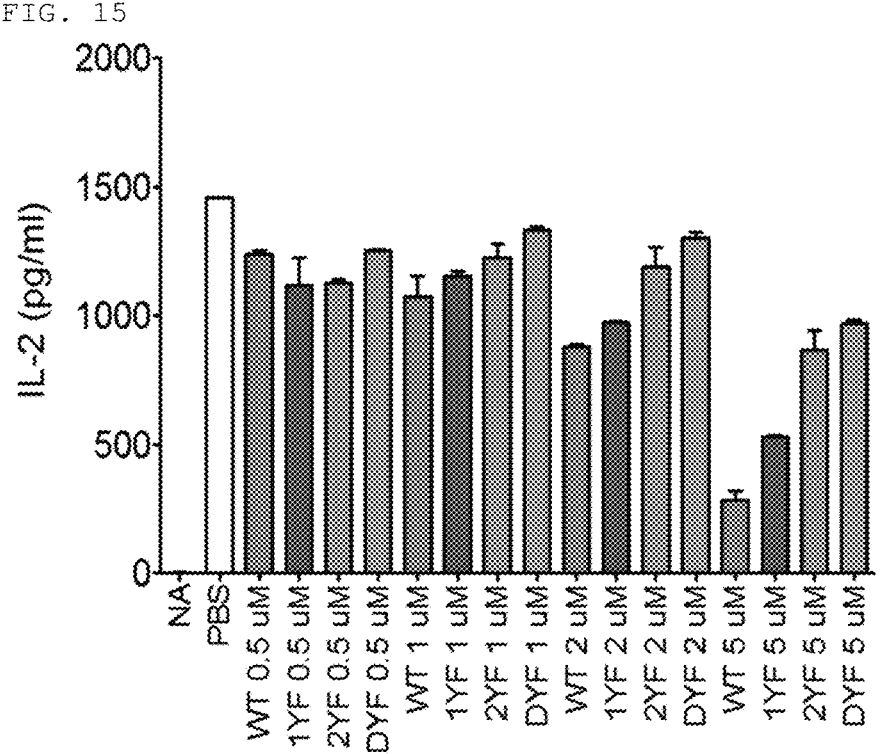
FIG. 15 is a graph showing measurement results of IL-2 expression inhibitory efficiencies of 0.5, 1, 2 or 5 µM WT, 1YF, 2YF and DYF. The numbers represent mean±s.e.m., and * represents $p<0.05$,  represents $p<0.01$, and * represents $p<0.001$; Student's t-test.

The spleen cells activated by the anti-CD3 and anti-CD28 antibodies were each treated with 0.5, 1, 2 or 5 µM WT, 1YF, 2YF and DYF, and IL-2 expression inhibitory abilities were measured by ELISA and are shown in FIG. 15.

At this time, the activated spleen cells were activated with anti-CD3/CD28 antibody in the presence of 1 µM PBS, 0.5, 1, 2 or 5 µM WT, 1YF, 2YF, DYF for 24 hours.

FIG. 15 is a graph showing measurement results of IL-2 expression inhibitory efficiencies of 0.5, 1, 2 or 5 µM WT, 1YF, 2YF and DYF. The numbers represent mean±s.e.m., and * represents p<0.05,  represents p<0.01, and * represents p<0.001; Student's t-test.

As can be seen from FIG. 15, 1YF, 2YF and DYF exhibited significant deterioration in IL-2 expression inhibitory efficiency, compared to WT. That is, it can be seen that the amino acid fragments of the ctCTTLA-4 peptide according to the present invention where 1Y and 2Y are located greatly contribute to inhibitory activity of IL-2 expression.

In other words, the ctCTLA-4 fragment peptides (Sequence ID Nos. 2 and 3) of areas including 1Y and 2Y amino acid residues also had excellent IL-2 expression inhibitory effect, like the present invention.

The test identified fragment peptides which were active in ctCTLA-4 and the following test was conducted using the fusion peptide (Sequence ID No. 4) created by fusing fragment peptides of ctCTLA-4.

2) Confirmation of Inhibition of dNP2-TAMRA, dNP2-ctCTLA-4 Fusion Product and dNP2-ctCTLA-4-fm3 Fusion Product on Activation of CD4 T-Cells in Mouse Model The present test was conducted to check whether or not the dNP2-TAMRA, dNP2-ctCTLA-4 fusion product and dNP2-ctCTLA-4-fm3 fusion product according to the present invention could inhibit activation of CD4 T-cells in the mouse model.

At this time, CD25 was an activation marker which has an increasing expression level when T-cells were activated, and whether or not activation of CD4 T-cells was inhibited based on the amount of expressed CD25 was determined.

Specifically, the test method was as follows.

A 96-well plate was coated with 0.1 µg of anti-CD3 and anti-CD28 antibodies in a cell incubator at 37° C. under 0.5% carbon dioxide for 5 hours. Then, isolated spleen cells of mice were seeded in a density of $2.5 \times 10^5$ on each well. The cells were treated with PBS or 0.1, 0.5, 1, 2 or 5 µM dNP2-TAMRA, dNP2-ctCTLA-4 or dNP2-ctCTLA-4-Fm, and then cultured in a cell incubator at 37° C. under 0.5% carbon dioxide for 24 hours. Then, the cells were stained with APC fluorescence-conjugated anti-CD4 mAb and PE fluorescence-fused anti-CD25 mAb at 4° C. for 20 minutes. Then, the cells produced through the aforementioned process were analyzed by a flow cytometer (FACS) to compare amounts of expressed CD25.

Figure 16:
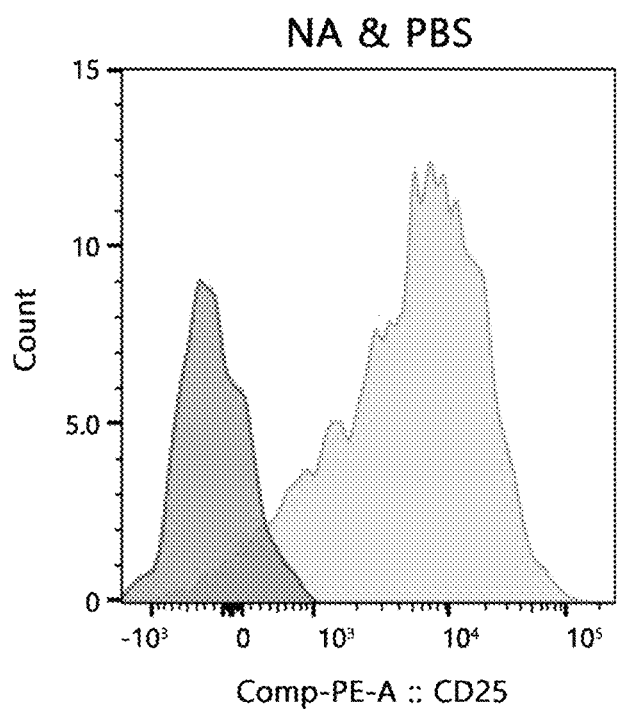
FIG. 16 is a graph showing introduction efficiency in primary mouse CD4-T-cells treated with only PBS.

FIG. 16 is a graph showing introduction efficiency of primary mouse CD4-T-cells (NA&PBS) treated with NA or PBS, and FIG. 17 is a graph showing intracellular transfer efficiencies of 0.1, 0.5, 1, 2 or 5 µM dNP2-TAMRA, dNP2-ctCTLA-4 fusion product and dNP2-ctCTLA-4-fm3 fusion product in primary mouse CD4-T-cells.

"NA", as herein used, means a Negative Control Group to which stimulus to activate T-cells was not applied and PBS herein used means a Positive Control Group to which stimuli of anti-CD3 and anti-CD28 monoclonal antibodies were applied to activate T-cells.

In FIG. 16, NA is indicated by a red graph and PBS is indicated by a blue graph. In this case, regarding PBS treatment, CD3 is a T cell receptor and CD28 is a co-receptor, monoclonal antibodies targeting them were used to apply stimulus to the T cell receptor. 270

That is, as shown in FIG. 16, the graph of PBS treated with the T cell receptor showed a great increase in CD25 expression, while the NA graph showed maintenance in CD25 expression because no stimulus was applied.

As can be seen from FIG. 17, CD25 expression was inhibited in proportion to the concentration of dNP2-ctCTLA-4 when dNP2-ctCTLA-4 was treated at different concentrations, and the dNP2-ctCTLA-4-fm3 also exhibited efficacy similar thereto. On the other hand, dNP2-TAMRA could not inhibit CD25 expression because it had no activity like ctCTLA-4.

Furthermore, the dNP2-CTLA-4 fusion product could exhibit significant effects so long as it was used in a concentration of 2 µM or more, while the dNP2-ctCTLA-4-fm fusion product exhibited excellent intracellular transfer efficiency even in a concentration of 0.1 µM, like the dNP2-ctCTLA-4 fusion product.

Figure 18:
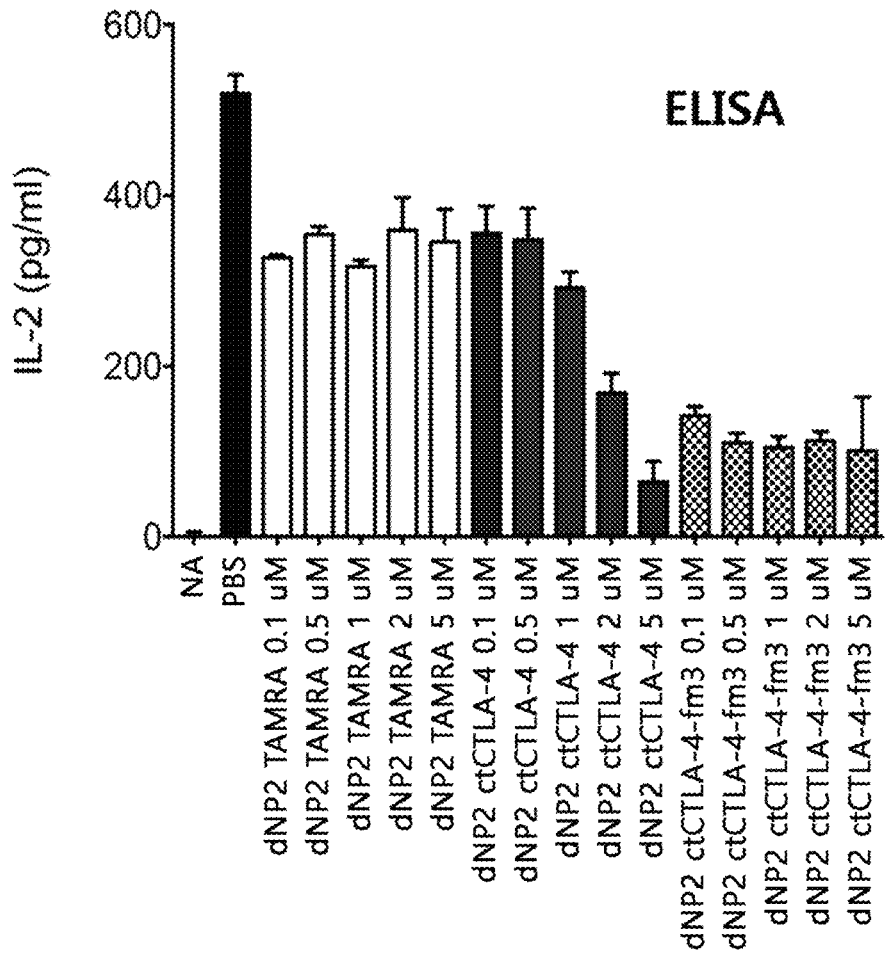
FIG. 18 is a graph showing IL-2 expression inhibitory efficiencies of 0.1, 0.5, 1, 2 or 5 µM dNP2-TAMRA fusion product, dNP2-CTLA-4 fusion product and dNP2-ctCTLA-4-fm3 fusion product. The numbers represent mean±s.e.m., and * represents p<0.05,  represents p<0.01, and * represents p<0.001; Student's t-test.

3) Evaluation of IL-2 Expression Inhibitory Abilities of Other Kinds of ctCTLA-4 Proteins The spleen cells activated by anti-CD3 and anti-CD28 antibodies were each treated with 0.1, 0.5, 1, 2 or 5 µM dNP2-TAMRA fusion product, dNP2-CTLA-4 fusion product and dNP2-ctCTLA-4-fm3 fusion product, and IL-2 expression inhibitory efficiency was measured by ELISA and is shown in FIG. 18.

At this time, the activated spleen cells were activated with the anti-CD3/CD28 antibody in the presence of 1 µM PBS, 0.1, 0.5, 1, 2 or 5 µM dNP2-TAMRA fusion product, dNP2-CTLA-4 fusion product and dNP2-ctCTLA-4-fm3 fusion product for 24 hours.

FIG. 18 is a graph showing IL-2 expression inhibitory efficiencies of 0.1, 0.5, 1, 2 or 5 µM dNP2-TAMRA fusion product, dNP2-CTLA-4 fusion product and dNP2-ctCTLA-4-fm3 fusion product. The numbers represent mean±s.e.m., and * represents $p<0.05$,  represents $p<0.01$, and * represents $p<0.001$; Student's t-test.

The results shown in FIG. 18 were very similar to those shown in FIG. 14. Specifically, the dNP2-TAMRA fusion product could never inhibit IL-2 expression.

In addition, the dNP2-CTLA-4 fusion product also exhibited inhibitory effect of IL-2 expression, but the effect was significant only at 2 µM or more.

Finally, the dNP2-ctCTLA-4-fm fusion product, which was obtained using fragments of ctCTLA-4 according to the present invention, exhibited excellent IL-2 expression effect, comparable to the dNP2-ctCTLA-4-fusion protein of Example 2.

CONCLUSION

The ctCTLA-4 peptide of Example 1 according to the present invention exhibited immune regulatory functions in transgenic NOD mice, regardless of B7 linkage. In particular, the present invention found that CTLA-4 (ctCTLA-4) has the function of encoding only a part of the exon 4 in CTLA-4 genes, independent of B7.

¼ CTLA-4, another analogue protein of CTLA-4, which is genetically similar to ctCTLA-4, had been conventionally found to strengthen T cell activation and promote autoimmunity (Liu, S. M. et al. Overexpression of the Ctla-4 isoform lacking exons 2 and 3 causes autoimmunity. Journal of immunology 188, 155-162, doi:10.4049/jimmunol.1102042 (2012); Ichinose, K. et al. Brief report: increased expression of a short splice variant of CTLA-4 exacerbates lupus in MRL/lpr mice. Arthritis and rheumatism 65, 764-769, doi:10.1002/art.37790 (2013)). However, alternative splicing of ¼ CTLA-4 induces frame-shift, which causes an amino acid sequence which is totally different from ctCTLA-4 (Ichinose, K. et al. Brief report: increased expression of a short splice variant of CTLA-4 exacerbates lupus in MRL/lpr mice. Arthritis and rheumatism 65, 764-769, doi:10.1002/art.37790 (2013); Ueda, H. et al. Association of the T-cell regulatory gene CTLA4 with susceptibility to autoimmune disease. Nature 423, 506-511, doi:10.1038/nature01621 (2003)).

In addition, a fusion protein wherein the ctCTLA-4 protein according to the present invention is fused with the cell-penetrating peptide was identified, which inhibited T cell activation and exhibited potent therapeutic effects in an autoimmune encephalomyelitis model. This suggests that the level of CTLA-4 cytoplasmic domain in T-cells plays an important role in functions thereof.

It could be seen that, although the dNP2-ctCTLA-4 fusion product could be transferred to giant cells and dendritic cells, significant variation in production of inflammatory cytokine by stimuli of toll-like receptor (TLR) ligands was not observed in such cells, while production of IL-2 and IFN-γ was successfully inhibited by activated CD4 and CD8 T-cells.

This means that the inhibitory mechanism against EAE that the fusion product according to the present invention had was not mediated by inhibiting functions of effecter T-cells, not innate immune cells.

Furthermore, in vivo tests according to the present invention showed that clinical symptoms were improved, when treated with the dNP2-ctCTLA-4 fusion product, even after the tail in the animal model was paralyzed, which demonstrated that the fusion product according to the present invention had potent preventive or therapeutic effects.

This means that inhibition of effecter T-cell functions by the dNP2-ctCTLA-4 fusion product according to the present invention can regulate progression of disease symptoms or promote recovery without significant in vivo toxicity.

In summary, the present invention developed the novel effective ctCTLA-4 peptides as well as fusion products wherein the ctCTLA-4 peptides are bound to the cell-penetrating peptide and verified that these peptides or fragments thereof or fusion products can be transferred to the brain and spinal cord.

It could be confirmed that novel treatment methods based on the technology of transfer to CNS-invasive T-cells using ctCTLA-4 peptides as well as fusion products wherein the ctCTLA-4 peptides are linked to the cell-penetrating peptide according to the present invention could be effective for controlling multiple sclerosis, in particular, the dNP2-ctCTLA-4 fusion product had the best optimal efficiency and stability.

INDUSTRIAL APPLICABILITY

The peptide produced according to the present invention can exert efficient therapeutic effects in spite of being used in low contents owing to the function to highly efficiently penetrate the blood-brain barrier and the blood-spinal cord barrier of the central nervous system, which could not be significantly permeated in the past, thus being applicable to various substances for preventing or treating central nervous system diseases.

The invention claimed is:

1. A peptide comprising a fusion peptide of two or more fragments of cytoplasmic domain in a cytotoxic T lymphocyte antigen-4 (CTLA-4) protein, said fusion peptide comprising the amino acid sequence of SEQ ID NO: 4.

2. A fusion product comprising,
   (a) a peptide comprising the amino acid sequence of SEQ ID NO: 4; and
   (b) a cell-penetrating peptide.

3. The fusion product according to claim 2, wherein the cell-penetrating peptide comprises any one selected from the group consisting of HIV-1 tat (47-57), D-amino acid-substituted HIV-1 tat (47-57), arginine-substituted HIV-1 tat (47-57), *Drosophila* Antennapaedia (43-58), a virus RNA-bound peptide including 7 or more amino acids, a DNA-bound peptide including 7 or more arginines, a polyarginine polypeptide including 6 to 8 arginines, a polypeptide including 7 to 11 lysines, a dNP2 protein comprising the amino acid sequence of SEQ ID NO: 5, Hph-1 (SEQ ID NO: 6), Transportan (SEQ ID NO: 8), PEP-1 (SEQ ID NO: 9), pVEC (SEQ ID NO: 10), M918 (SEQ ID NO: 11), TP10 (SEQ ID NO: 12), VP22 (SEQ ID NO: 13), Buforin 2 (SEQ ID NO: 14), KALA (SEQ ID NO: 15), CL22 (SEQ ID NO: 16), and Crotamine (SEQ ID NO: 17).

4. The fusion product according to claim 2, wherein the cell-penetrating peptide is a dNP2 protein of the amino acid sequence of SEQ ID NO: 5.

5. A pharmaceutical composition comprising the fusion product according to claim 2 as an active ingredient.

6. The pharmaceutical composition according to claim 5, wherein the cell-penetrating peptide in the fusion product has an activity to penetrate the blood-brain barrier or blood-spinal cord barrier.

7. A method for treating multiple sclerosis in a subject in need thereof, comprising administering the pharmaceutical composition according to claim 5 to the subject.

8. The method according to claim 7, wherein the cell-penetrating peptide comprises any one selected from the group consisting of HIV-1 tat (47-57), D-amino acid-substituted HIV-1 tat (47-57), arginine-substituted HIV-1 tat (47-57), *Drosophila* Antennapaedia (43-58), a virus RNA-bound peptide including 7 or more amino acids, a DNA-bound peptide including 7 or more arginines, a polyarginine polypeptide including 6 to 8 arginines, a polypeptide including 7 to 11 lysines, a dNP2 protein comprising the amino acid sequence of SEQ ID NO: 5, Hph-1 (SEQ ID NO: 6), Transportan (SEQ ID NO: 8), Pep-1 (SEQ ID NO: 9), pVEC (SEQ ID NO: 10), M918 (SEQ ID NO: 11), TP10 (SEQ ID NO: 12), VP22 (SEQ ID NO: 13), Buforin 2 (SEQ ID NO: 14), KALA (SEQ ID NO: 15), CL22 (SEQ ID NO: 16), and Crotamine (SEQ ID NO: 17).

* * * * *

SEQUENCE LISTING

<160> NUMBER OF SEQ ID NOS: 23

<210> SEQ ID NO 1
<211> LENGTH: 36
<212> TYPE: PRT
<213> ORGANISM: Artificial Sequence
<220> FEATURE:
<223> OTHER INFORMATION: Synthetic

<400> SEQUENCE: 1

Lys Met Leu Lys Lys Arg Ser Pro Leu Thr Thr Gly Val Tyr Val Lys
1               5                   10                  15

Met Pro Pro Thr Glu Pro Glu Cys Glu Lys Gln Phe Gln Pro Tyr Phe
            20                  25                  30

Ile Pro Ile Asn
        35

<210> SEQ ID NO 2
<211> LENGTH: 10
<212> TYPE: PRT
<213> ORGANISM: Artificial Sequence
<220> FEATURE:
<223> OTHER INFORMATION: Synthetic

<400> SEQUENCE: 2

Tyr Val Lys Met Pro Pro Thr Glu Pro Glu
1               5                   10

<210> SEQ ID NO 3
<211> LENGTH: 6
<212> TYPE: PRT
<213> ORGANISM: Artificial Sequence
<220> FEATURE:
<223> OTHER INFORMATION: Synthetic

<400> SEQUENCE: 3

Tyr Phe Ile Pro Ile Asn
1               5

<210> SEQ ID NO 4
<211> LENGTH: 16
<212> TYPE: PRT
<213> ORGANISM: Artificial Sequence
<220> FEATURE:
<223> OTHER INFORMATION: Synthetic

<400> SEQUENCE: 4

Tyr Val Lys Met Pro Pro Thr Glu Pro Glu Tyr Phe Ile Pro Ile Asn
1               5                   10                  15

<210> SEQ ID NO 5
<211> LENGTH: 24
<212> TYPE: PRT
<213> ORGANISM: Artificial Sequence
<220> FEATURE:
<223> OTHER INFORMATION: Synthetic

<400> SEQUENCE: 5

Lys Ile Lys Lys Val Lys Lys Lys Gly Arg Lys Gly Ser Lys Ile Lys
1               5                   10                  15

Lys Val Lys Lys Lys Gly Arg Lys
            20

<210> SEQ ID NO 6
<211> LENGTH: 11

```
<212> TYPE: PRT
<213> ORGANISM: Artificial Sequence
<220> FEATURE:
<223> OTHER INFORMATION: Synthetic

<400> SEQUENCE: 6

Tyr Ala Arg Val Arg Arg Gly Pro Arg Arg
1               5                   10

<210> SEQ ID NO 7
<211> LENGTH: 11
<212> TYPE: PRT
<213> ORGANISM: Artificial Sequence
<220> FEATURE:
<223> OTHER INFORMATION: Synthetic

<400> SEQUENCE: 7

Tyr Gly Arg Lys Lys Arg Arg Gln Arg Arg
1               5                   10

<210> SEQ ID NO 8
<211> LENGTH: 27
<212> TYPE: PRT
<213> ORGANISM: Artificial Sequence
<220> FEATURE:
<223> OTHER INFORMATION: Synthetic

<400> SEQUENCE: 8

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 9
<211> LENGTH: 21
<212> TYPE: PRT
<213> ORGANISM: Artificial Sequence
<220> FEATURE:
<223> OTHER INFORMATION: Synthetic

<400> SEQUENCE: 9

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 10
<211> LENGTH: 18
<212> TYPE: PRT
<213> ORGANISM: Artificial Sequence
<220> FEATURE:
<223> OTHER INFORMATION: Synthetic

<400> SEQUENCE: 10

Leu Leu Ile Ile Leu Arg Arg Arg Ile Arg Lys Gln Ala His Ala His
1               5                   10                  15

Ser Lys

<210> SEQ ID NO 11
<211> LENGTH: 22
<212> TYPE: PRT
<213> ORGANISM: Artificial Sequence
<220> FEATURE:
<223> OTHER INFORMATION: Synthetic

<400> SEQUENCE: 11
```

```
Met Val Thr Val Leu Phe Arg Arg Leu Arg Ile Arg Arg Ala Cys Gly
1               5                   10                  15

Pro Pro Arg Val Arg Val
            20
```

<210> SEQ ID NO 12
<211> LENGTH: 21
<212> TYPE: PRT
<213> ORGANISM: Artificial Sequence
<220> FEATURE:
<223> OTHER INFORMATION: Synthetic

<400> SEQUENCE: 12

```
Ala Gly Tyr Leu Leu Gly Lys Ile Asn Leu Lys Ala Leu Ala Ala Leu
1               5                   10                  15

Ala Lys Lys Ile Leu
            20
```

<210> SEQ ID NO 13
<211> LENGTH: 34
<212> TYPE: PRT
<213> ORGANISM: Artificial Sequence
<220> FEATURE:
<223> OTHER INFORMATION: Synthetic

<400> SEQUENCE: 13

```
Asp Ala Ala Thr Ala Thr Arg Gly Arg Ser Ala Ala Ser Arg Pro Thr
1               5                   10                  15

Glu Arg Pro Arg Ala Pro Ala Arg Ser Ala Ser Arg Pro Arg Arg Pro
            20                  25                  30

Val Glu
```

<210> SEQ ID NO 14
<211> LENGTH: 20
<212> TYPE: PRT
<213> ORGANISM: Artificial Sequence
<220> FEATURE:
<223> OTHER INFORMATION: Synthetic

<400> SEQUENCE: 14

```
Thr Arg Ser Ser Arg Ala Gly Leu Gln Phe Pro Val Gly Arg Val His
1               5                   10                  15

Arg Leu Leu Arg
            20
```

<210> SEQ ID NO 15
<211> LENGTH: 30
<212> TYPE: PRT
<213> ORGANISM: Artificial Sequence
<220> FEATURE:
<223> OTHER INFORMATION: Synthetic

<400> SEQUENCE: 15

```
Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30
```

<210> SEQ ID NO 16
<211> LENGTH: 35
<212> TYPE: PRT
<213> ORGANISM: Artificial Sequence
<220> FEATURE:

<223> OTHER INFORMATION: Synthetic

<400> SEQUENCE: 16

Lys Lys Lys Lys Lys Lys Gly Gly Phe Leu Gly Phe Trp Arg Gly Glu
1               5                   10                  15

Asn Gly Arg Lys Thr Arg Ser Ala Tyr Glu Arg Met Cys Asn Ile Leu
            20                  25                  30

Lys Gly Lys
        35

<210> SEQ ID NO 17
<211> LENGTH: 42
<212> TYPE: PRT
<213> ORGANISM: Artificial Sequence
<220> FEATURE:
<223> OTHER INFORMATION: Synthetic

<400> SEQUENCE: 17

Tyr Lys Gln Cys His Lys Lys Gly Gly His Cys Phe Pro Lys Glu Lys
1               5                   10                  15

Ile Cys Leu Pro Pro Ser Ser Asp Phe Gly Lys Met Asp Cys Arg Trp
            20                  25                  30

Arg Trp Lys Cys Cys Lys Lys Gly Ser Gly
        35                  40

<210> SEQ ID NO 18
<211> LENGTH: 67
<212> TYPE: DNA
<213> ORGANISM: Artificial Sequence
<220> FEATURE:
<223> OTHER INFORMATION: Primer

<400> SEQUENCE: 18
aagattaaga aagtcaagaa gaaaggaaga aaggaattct acccatacga tgttccagat      60
tacgcta                                                                67

<210> SEQ ID NO 19
<211> LENGTH: 67
<212> TYPE: DNA
<213> ORGANISM: Artificial Sequence
<220> FEATURE:
<223> OTHER INFORMATION: Primer

<400> SEQUENCE: 19
gctagcaaga ttaagaaagt caagaagaaa ggaagaaagg atccaagat taagaaagtc      60 aagaaga                                                                67

<210> SEQ ID NO 20
<211> LENGTH: 73
<212> TYPE: DNA
<213> ORGANISM: Artificial Sequence
<220> FEATURE:
<223> OTHER INFORMATION: Primer

<400> SEQUENCE: 20
gctagctatg gacgcaagaa gcgccgccag cgccgccgcg gatcctaccc atacgatgtt      60
ccagattacg cta                                                         73

<210> SEQ ID NO 21
<211> LENGTH: 67
<212> TYPE: DNA
<213> ORGANISM: Artificial Sequence -continued

```
<220> FEATURE:
<223> OTHER INFORMATION: Primer

<400> SEQUENCE: 21
tatgcgcgtg tgcgacgtcg tggcccacgt cgaggatcct acccatacga tgttccagat    60
tacgcta                                                              67

<210> SEQ ID NO 22
<211> LENGTH: 61
<212> TYPE: DNA
<213> ORGANISM: Artificial Sequence
<220> FEATURE:
<223> OTHER INFORMATION: Primer

<400> SEQUENCE: 22
aagattaaga aagtcaagaa gaaaggaaga aaggtgagca agggcgagga gctgttcacc    60
g                                                                    61

<210> SEQ ID NO 23
<211> LENGTH: 67
<212> TYPE: DNA
<213> ORGANISM: Artificial Sequence
<220> FEATURE:
<223> OTHER INFORMATION: Primer

<400> SEQUENCE: 23
gctagcaaga ttaagaaagt caagaagaaa ggaagaaagg gatccaagat taagaaagtc    60
aagaaga                                                              67
```